US009034630B2

(12) United States Patent
Gorvel et al.

(10) Patent No.: US 9,034,630 B2
(45) Date of Patent: May 19, 2015

(54) MODIFIED GRAM-NEGATIVE BACTERIA FOR USE AS VACCINES

(71) Applicants: Institut National de la Sante et de la Recherche Medicale (INSERM), Paris (FR); Centre National de la Recherche Scientifique—CNRS, Paris (FR); Universite de la Mediterranee—Aix-Marseille II, Marseilles (FR); Universidad de Navarra, Pamplona (ES)

(72) Inventors: Jean-Pierre Gorvel, Marseille Cedex (FR); Vilma Arce Gorvel, Marseille Cedex (FR); Maite Iriarte, Pamplona (ES); Ignacio Moriyon, Pamplona (ES); Raquel Conde-Alvarez, Pamplona (ES)

(73) Assignees: Institut National de la Sante et de la Recherche Medicale (INSERM), Paris (FR); Centre National de la Recherche Scientifique—CNRS, Paris (FR); Université d'Aix Marseille, Marseilles (FR); UNIVERSIDAD DE NAVARRA, Pamplona (ES)

( * ) Notice: Subject to any disclaimer, the term of this patent is extended or adjusted under 35 U.S.C. 154(b) by 0 days.

(21) Appl. No.: 14/296,495

(22) Filed: Jun. 5, 2014

(65) Prior Publication Data
US 2014/0286996 A1 Sep. 25, 2014

Related U.S. Application Data

(63) Continuation-in-part of application No. 13/496,007, filed as application No. PCT/EP2010/063921 on Sep. 21, 2010, now Pat. No. 8,778,655.

(30) Foreign Application Priority Data

Sep. 21, 2009 (EP) .................................... 09305879

(51) Int. Cl.
C12N 1/20 (2006.01)
C12N 15/00 (2006.01)
A61K 39/10 (2006.01)
A61K 39/39 (2006.01)
A61K 39/02 (2006.01)
A61K 39/00 (2006.01)

(52) U.S. Cl.
CPC ............... *A61K 39/39* (2013.01); *A61K 39/098* (2013.01); *A61K 2039/522* (2013.01); *A61K 2039/552* (2013.01)

(58) Field of Classification Search
None
See application file for complete search history.

(56) References Cited

U.S. PATENT DOCUMENTS 6,444,445 B2 9/2002 Nikolich et al.

FOREIGN PATENT DOCUMENTS

| CN | 101386831 | 3/2009 |
| WO | 93/16728 | 9/1993 |
| WO | 2008-095679 | 8/2008 |

OTHER PUBLICATIONS

Saleem et al. Veterinary Microbiology vol. 140, issue 3-4, Jan. 27, 2010, pp. 392-398.*
Soler-Llorens et al. Veterinary Research 2014, 45:72.*
Monreal et al. Infection and Immunity, Jun. 2003, p. 3261-3271 vol. 71, No. 6.*
Velasco et al.; "*Brucella abortus* and Its Closes Phylogenetic Relative, *Ochrobactrum* spp., Differ in Outer Membrane Permeability and Cationic Peptide Resistance"; Infection and Immunity, Jun. 2000, pp. 3210-3218.
Martinez De Tejada et al.; "The Outer Membranes of *Brucella* spp. Are Resistant to Bactericidal Cationic Peptides"; Infection and Immunity, Aug. 1995, pp. 3054-3061.
Gonzalez et al.; "Burcellosis Vaccines: Assessment of *Brucella melitensis* Lipopolysaccharide Rough Mutants Defective in Core and O-Polysaccharide Synthesis and Export"; PLoS One, vol. 3, issue 7, Jul. 2008, pp. 1-15.
Kohler et al.; "The Analysis of the Intramacrophagic Virulome of *Brucella* suis Deciphers the Environment Encountered by the Pathogen Inside the Macrophage Host Cell"; Proceedings of the National Academy of Sciences of the United States of America, vol. 99, No. 24, Nov. 26, 2002, pp. 15711-15716.
Delrue et al.; "*Brucella* Pathogenesis, Genes Identified from Random Large-Scale Screens"; FEMS Microbiology Letters, vol. 231, No. 1, Feb. 9, 2004, pp. 1-12.
Database UniProt (Online), Jul. 19, 2004, "SubName: Full=Lipopolysaccharide core biosynthesis mannosyltransferase 1pcC;" XP-002573333, retrieved from EBI accession No. Uniprot:Q6FZ58, database accession No. Q6FZ58; the whole document.
Uniprot accession No. C4IPI5 Jul. 7, 2009.
Uniprot accession No. C4ISH8 Jul. 7, 2009.
Uniprot accession No. Q8YID5 Mar. 1, 2002.
Kohler et al. PNAS, vol. 99, No. 24, 26 Nov. 2002, pp. 15711-15716.

* cited by examiner

*Primary Examiner* — Oluwatosin Ogunbiyi
(74) *Attorney, Agent, or Firm* — Whitham Curtis Christofferson & Cook, PC

(57) ABSTRACT

The invention relates to Gram-negative bacteria carrying an inactivated gene encoding a glycosyltransferase involved in the synthesis of the core of the LPS of said Gram-negative bacteria, wherein said inactivated gene results in the synthesis of a LPS having a modified core. These strains have an attenuated virulence but induce a humoral immunity sufficient for ensuring vaccination of the host.

5 Claims, 9 Drawing Sheets

MODIFIED GRAM-NEGATIVE BACTERIA FOR USE AS VACCINES

Cross-Reference to Related Applications

This application is a divisional application of USSN 13/496,007, filed Apr. 10, 2012, which is a Rule 371 application of PCT/EP2010/063921 filed Sep. 21, 2010.

FIELD OF THE INVENTION

The invention generally relates to the field of modified gram-negative bacteria for use as vaccines.

BACKGROUND OF THE INVENTION

Gram-negative bacteria are those bacteria that do not retain crystal violet dye in the Gram staining protocol. Many species of Gram-negative bacteria are pathogenic, meaning that they can cause disease in a host organism. This pathogenic capability is usually associated with certain components of Gram-negative cell walls, in particular the lipopolysaccharide (also known as LPS or endotoxin) layer. LPS is a major component of the outer membrane of Gram-negative bacteria, contributing greatly to the structural integrity of the bacteria, and protecting the membrane from certain kinds of chemical attack. LPS also increases the negative charge of the cell membrane and helps stabilize the overall membrane structure. LPS is an endotoxin, and induces a strong response from normal animal immune systems. LPS is additionally an exogenous pyrogen (external fever-inducing compound). LPS comprises three parts: polysaccharide (O) side chains, a core polysaccharide and lipid A.

Lipid A contains unusual fatty acids (e.g. hydroxy-myristic acid) and is embedded in the outer membrane while the rest of the LPS projects from the surface. Lipid A is a disaccharide with multiple fatty acid tails reaching into the membrane. When bacterial cells are lysed by the immune system, fragments of membrane containing lipid A are released into the circulation, causing fever, diarrhea, and possible fatal endotoxic shock (also called septic shock).

The polysaccharide side chain is referred to as the O-antigen of the bacteria. O side chain (O-antigen) is a polysaccharide chain that extends from the core polysaccharide. The composition of the O side chain varies between different Gram-negative bacterial strains. O side chains are easily recognized by the antibodies of the host, however, the nature of the chain can easily be modified by Gram-negative bacteria to avoid detection.

The core oligosaccharide contains unusual sugars (e.g. KDO, keto-deoxyoctulosonate and heptose), but little is known concerning its role. In particular, its role in virulence has never been studied directly.

Numerous LPS mutants inducing humoral immunity to lipopolysaccharide (LPS) have been proposed as potential vaccines. However, pure LPS mutants or bacteria expressing LPS mutants are generally considered too toxic to be used as vaccines, in particular in view of their strong adverse effects, and there is thus a need for new vaccines, presenting an attenuated virulence and inducing a sufficient humoral immunity for ensuring vaccination of the host.

SUMMARY OF THE INVENTION

The inventors have found that, by modifying a particular structure of the core of the LPS of Gram-negative bacteria, it is possible to obtain strains having an attenuated virulence but inducing a humoral immunity sufficient for ensuring vaccination of the host. Indeed, the inventors have discovered that particular glycosyltransferases involved in the synthesis of the core of the LPS have a critical role in Gram-negative bacteria virulence. When at least one of these glycosyltransferases is inactivated, the modified LPS synthesized by the Gram-negative bacteria induce a strong immune response of the host and its vaccination. Moreover, the inventors have further shown that the administration to a host of a LPS produced by Gram-negative bacteria wherein at least one of said glycosyltransferases is inactivated induces an unspecific immune response and can thus be used as an adjuvant for stimulating the immune system.

DETAILED DESCRIPTION OF THE INVENTION

An object of the invention concerns a Gram-negative bacterium carrying an inactivated gene encoding a glycosyltransferase involved in the synthesis of the core of the LPS of said Gram-negative bacterium, wherein said glycosyltransferase is selected from the group comprising the glycosyltransferases having the amino acid sequence of SEQ ID NO:1 or SEQ ID NO:21, or homologues thereof having an amino acid sequence having at least 50%, particularly at least 60%, more particularly at least 70%, most particularly at least 80% of identity with SEQ ID NO:1 or SEQ ID NO:21, and wherein said inactivated gene encoding a glycosyltransferase involved in the synthesis of the core of the LPS of said Gram-negative bacterium results in the synthesis of a LPS having a modified core.

The inventors have shown that the glycosyltransferase having the amino acid sequence of SEQ ID NO:1 is a glycosyltransferase involved in the synthesis of a particular branched structure of the core of the LPS of *Brucella abortus*. This glycosyltransferase has been called BABLpcC by the inventors. In particular, the inventors have shown that, contrary to all mutants of the LPS core described to date which induce the deletion of the core and of the O-chain of the LPS (Gonzales et al.; PLOS one, July 2008, vol. 3, issue 7, e2760), the mutant Gram-negative bacteria according to the invention present a LPS which lacks part of the core but keeps an intact O-chain. These results evidence that *Brucella abortus* possesses a branched LPS core, which was unknown to date (see FIG. 10, which gives a proposed structure of the core of the LPS of *Brucella abortus*). Without wanting to be bound by a theory, it is believed that this branched structure of core of the LPS in the wild type bacteria is important in avoiding recognition by innate immunity. Consequently, the Gram negative bacteria mutants according to the invention trigger a more intense and protective immune response, and thus constitute very promising vaccines.

In addition to the BABLpcC of *Brucella abortus*, the inventors have also shown that homologous glycosyltransferases exist in other organisms. As a result, it is highly credible that the particular structure of the core of the LPS of *Brucella abortus* exists in other organism. The inventors have further shown that these homologous proteins have an amino acid sequence presenting a high percentage of identity with SEQ ID NO:1, of at least 60%, particularly of at least 70%, more particularly of at least 80%.

Examples of glycosyltransferases involved in the synthesis of the core of the LPS and having a high percentage of identity with BABLpcC are presented in the table hereinafter:

| Organism | SEQ ID NO: | % identity with SEQ ID NO: 1 |
|---|---|---|
| Bartonella quintana | 2 | 65 |
| Bartonella tribocorum | 3 | 64 |
| Bartonella bacilliformis | 4 | 61 |
| Ochrobactrum anthropi | 5 | 85 |
| Ochrobactrum intermedium | 6 | 85 |
| Agrobacterium tumefaciens | 7 | 63 |
| Bartonella henselae | 22 | 69 |

Hence, in a particular embodiment, the invention also concerns the gram-negative bacterium according to the invention wherein said amino acid sequence having at least 60%, particularly at least 70%, more particularly at least 80% of identity with SEQ ID NO: 1 is selected from the group comprising SEQ ID NO:2, SEQ ID NO:3, SEQ ID NO:4, SEQ ID NO:5, SEQ ID NO:6, SEQ ID NO:7 and SEQ ID NO:22.

In addition to the glycosyltransferase of SEQ ID NO:1, the inventors have shown that another glycosyltransferase, having the sequence of SEQ ID NO:21, is also involved in the synthesis of the branched structure of the core of the LPS of a Gram-negative bacterium, *Brucella abortus*. The inventors have also shown that homologous glycosyltransferases exist in other organisms, as previously described for BABLpcC. The inventors have further shown that these homologous proteins have an amino acid sequence presenting a percentage of identity with SEQ ID NO:21 of at least 50%, particularly of at least 60%, more particularly of at least 62%.

Examples of glycosyltransferases involved in the synthesis of the core of the LPS and having a percentage of identity with SEQ ID NO:21 of at least 50%, particularly of at least 60%, more particularly of at least 62% are presented in the table hereinafter:

| Organism | SEQ ID NO: | % identity with SEQ ID NO: 21 |
|---|---|---|
| Ochrobactrum anthropi | 23 | 62 |
| Ochrobactrum intermedium | 24 | 62 |
| Agrobacterium radiobacter | 25 | 57 |

In another particular embodiment, the invention also concerns the Gram-negative bacteria according to the invention wherein a gene encoding a protein involved in the synthesis of the O-polysaccharide of the LPS is inactivated. Indeed, in addition to the inactivation of genes encoding glycosyltransferases involved in the synthesis of the branched structure of the core of the LPS, it is of interest to inactivate genes involved in the synthesis of the O-polysaccharide of the LPS. Such a "double mutant", lacking the branched structure of the core and partially or totally lacking the O-chain, is useful for distinguishing animals that are vaccinated with it and animals that are infected with the naturally occurring Gram-negative bacterium (wild type), as explained hereafter in the description.

Examples of genes encoding a protein involved in the synthesis of the O-polysaccharide of the LPS are wboB, wboA, wbkE, wbkA, gmd, per, wzm, wzt, wbkB, wbkC, wbkF and wbkD (Gonzales et al.; PLOS one, July 2008, vol. 3, issue 7, e2760). Their SEQ IDs are given in the table hereinafter:

| Gene name | Predicted protein function | Amino acid SEQ ID |
|---|---|---|
| wboB | Mannosyl (perosaminyl) transferase | 8 |
| wboA | Mannosyl (perosaminyl) transferase | 9 |
| wbkE | Mannosyl (perosaminyl) transferase | 10 |
| wbkA | Mannosyl (perosaminyl) transferase | 11 |
| gmd | GDP-mannose dehydratase | 12 |
| per | Perosamine synthetase | 13 |
| wzm | ABC transporter | 14 |
| wbkF | Undecaprenyl-glycosyltransferase | 15 |
| wbkD | Epimerase/dehydratase | 16 |
| wzt | ABC transporter | 26 |
| wbkB | Synthetase | 27 |
| wbkC | Formyltransferase | 28 |

Accordingly, in an embodiment of the invention, said protein involved in the synthesis of the O-polysaccharide of the LPS is thus selected from the group comprising the proteins having the amino acid sequence of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:26, SEQ ID NO:27 and SEQ ID NO:28 or homologues thereof having an amino acid sequence having at least 50%, particularly at least 60%, more particularly at least 70%, still particularly at least 80% and most particularly at least 90% of identity with an amino acid sequence selected from the group comprising SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:26, SEQ ID NO:27 and SEQ ID NO:28. The choice of a percentage of identity of at least 50% is not arbitrary: this percentage of identity has been found by the inventors for the homologous sequences of SEQ ID NO:8-16, 26-28 in the particular strain *Yersinia enterocitica* O:9.

In a particular embodiment of the invention, said protein involved in the synthesis of the O-polysaccharide of the LPS is a perosamine synthetase having the amino acid sequence of SEQ ID NO:13 or a homologue thereof having an amino acid sequence having at least 90% of identity with the amino acid sequence of SEQ ID NO:13. This high percentage of identity (of at least 90%) is typically found in the strains of the genus *Brucella*.

According to the invention, by "inactivated gene" it is meant a gene that encodes either a non-functional protein or no protein at all. According to the invention the inactivation of a gene can be carried out by the various methods known by the skilled person. Examples of methods for inactivating a gene are the knock out, and particularly the directed mutagenesis or the homologous recombination, as described in Conde-Alvarez R. et al., Cell Microbial 2006 August; 8(8):1322-35. A particular method for inactivating a gene according to the invention is described in the experimental section.

In another particular embodiment of the invention, the Gram-negative bacteria according to the invention are selected from the group comprising the bacteria of the genus *Brucella*, *Bartonella*, *Ochrobactrum* and *Agrobacterium*.

In a particular embodiment, the invention is directed to a bacterium of the genus *Brucella*, wherein said glycosyltransferase is selected from the group comprising the glycosyltransferases having the amino acid sequence of SEQ ID NO: 1 or SEQ ID NO:21, or homologues thereof having an amino acid sequence having at least 60%, particularly at least 70%, more particularly at least 80% of identity with SEQ ID NO:1 or SEQ ID NO:21.

Particular species of the genus *Brucella* according to the invention are *Brucella melitensis*, *Brucella abortus*, *Brucella suis*, *Brucella ovis*, *Brucella pinnipedialis*, *Brucella ceti*, *Brucella microti*, and *Brucella canis*.

Particular species of the genus *Ochrobactrum* according to the invention are *Ochrobactrum anthropi* and *Ochrobactrum intermedium*.

The invention further concerns in particular a *Ochrobactrum anthropi* bacterium, wherein said glycosyltransferase according to the invention is selected from the group comprising the glycosyltransferases having the amino acid sequence of SEQ ID NO:5 or an amino acid sequence having at least 85% of identity with SEQ ID NO:1, or having the amino acid sequence of SEQ ID NO:23 or an amino acid sequence having at least 62% of identity with SEQ ID NO:21.

The invention further concerns in particular a *Ochrobactrum intermedium* bacterium, wherein said glycosyltransferase according to the invention is selected from the group comprising the glycosyltransferases having the amino acid sequence of SEQ ID NO:6 or an amino acid sequence having at least 85% of identity with SEQ ID NO:1 or having the amino acid sequence of SEQ ID NO:24 or an amino acid sequence having at least 62% of identity with SEQ ID NO:21.

Particular species of the genus *Bartonella* according to the invention are *Bartonella henselae, Bartonella quintana, Bartonella tribocorum, Bartonella bacilliformis*. The invention also concerns in particular a *Bartonella henselae* bacterium, wherein said glycosyltransferase according to the invention is selected from the group comprising the glycosyltransferases having the amino acid sequence of SEQ ID NO:22, or an amino acid sequence having at least 69% of identity with SEQ ID NO:1.

The invention also concerns in particular a *Bartonella quintana* bacterium, wherein said glycosyltransferase according to the invention is selected from the group comprising the glycosyltransferases having the amino acid sequence of SEQ ID NO:2 or an amino acid sequence having at least 65% of identity with SEQ ID NO:1.

The invention still concerns in particular a *Bartonella tribocorum* bacterium, wherein said glycosyltransferase according to the invention is selected from the group comprising the glycosyltransferases having the amino acid sequence of SEQ ID NO:3, or an amino acid sequence having at least 64% of identity with SEQ ID NO:1.

The invention also concerns in particular a *Bartonella bacilliformis* bacterium, wherein said glycosyltransferase according to the invention is selected from the group comprising the glycosyltransferases having the amino acid sequence of SEQ ID NO:4, or an amino acid sequence having at least 61% of identity with SEQ ID NO:1.

Particular species of the genus *Agrobacterium* according to the invention are *Agrobacterium tumefaciens* and *Agrobacterium radiobacter*.

The invention thus concerns in particular an *Agrobacterium tumefaciens* bacterium, wherein said glycosyltransferase according to the invention is selected from the group comprising the glycosyltransferases having the amino acid sequence of SEQ ID NO:7 or an amino acid sequence having at least 63% of identity with SEQ ID NO:1.

The invention further concerns in particular an *Agrobacterium radiobacter* bacterium, wherein said glycosyltransferase according to the invention is selected from the group comprising the glycosyltransferases having the amino acid sequence of SEQ ID NO:25 or an amino acid sequence having at least 57% of identity with SEQ ID NO:21.

As used herein, the percentage of sequence identity refers to comparisons among amino acid sequences, and is determined by comparing two optimally aligned sequences over a comparison window, wherein the portion of the amino acid sequence in the comparison window may comprise additions or deletions (i.e., gaps) as compared to the reference sequence (which does not comprise additions or deletions) for optimal alignment of the two sequences. The percentage may be calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical amino acid residue occurs in both sequences or an amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. ScL USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTP program (for amino acid sequences) uses as defaults a wordlength (W) of 3, an expectation (E) of 10, and the BLOSUM62 scoring matrix (see Henikoff and Henikoff, 1989, Proc Natl Acad Sci USA 89: 10915). Exemplary determination of sequence alignment and % sequence identity can employ the BESTFIT or GAP programs in the GCG Wisconsin Software package (Accelrys, Madison Wis.), using default parameters provided.

The invention also concerns the therapeutic applications of the Gram-negative mutants according to the invention. In particular, the invention related to the gram-negative bacterium according to the invention for use in a method for treatment of the human or animal body.

In another aspect, the invention relates to vaccines comprising a gram-negative bacterium according to the invention. Indeed, the inventors have shown that the bacteria according to the invention can be used as live vaccines.

The invention thus relates to the gram-negative bacterium according to the invention, for use in a method for vaccinating the human or animal body against a disease caused by the wild type of said gram-negative bacterium.

The invention also relates to a method for treating, in particular vaccinating, a subject against a disease caused by a gram-negative bacterium, said method comprising the step of administering an therapeutically effective amount of said gram-negative bacterium modified according to the invention.

In the context of the invention, the term "treating" or "treatment", as used herein, means reversing, alleviating, inhibiting the progress of, or preventing the disorder or condition to which such term applies.

As used herein, "subject" refers to a human or animal that may benefit from the administration of a Gram-negative bacterium as recited herein.

By a "therapeutically effective amount" of a Gram-negative bacterium as described previously, is meant a sufficient amount to treat the disease, at a reasonable benefit/risk ratio applicable to any medical treatment.

A vaccine is defined herein as a biological agent which is capable of providing a protective response in an animal to which the vaccine has been delivered and is incapable of causing severe disease. The vaccine stimulates antibody production or cellular immunity against the pathogen causing the disease; administration of the vaccine thus results in immunity from the disease.

According to the invention, by a "wild type" it is meant a gram-negative bacterium wherein the previously described genes are active.

If desired, the live vaccines according to the invention may contain an adjuvant. Examples of suitable compounds and compositions with adjuvant activity are well known in the art. Furthermore, nucleic acid sequences encoding polypeptides for pharmaceutical or diagnostic applications, in particular immunomodulators such as lymphokines, interferons or cytokines, may be incorporated into the vaccine.

A vaccine according to the invention can be prepared by conventional methods such as those commonly used for the commercially available live attenuated vaccines. The vaccine may be administered by intramuscular, intradermal, subcutaneous or intranasal inoculation or injection in an amount which is effective to protect the animal against challenge by a virulent strain of Gram-negative bacterium. This amount may vary according to the animal being inoculated, taking into consideration the size and weight of the animal. The vaccine according to the invention comprises an effective dosage of the Gram-negative bacterium mutant as the active component, i.e. a sufficient amount of Gram-negative bacterium mutant that will induce immunity in the vaccinated animals, against challenge by the virulent Gram-negative bacterium. Immunity is defined herein as the induction of a significant higher level of protection in a population of animals against mortality and clinical symptoms after vaccination compared to an unvaccinated group. In particular, the vaccine according to the invention prevents a large proportion of vaccinated animals against the occurrence of clinical symptoms of the disease and mortality.

When providing a patient (human or animal) with live bacteria vaccines, the dosage of administered bacteria will vary depending upon such factors as the route of administration, patient's species, age, weight, height, sex, general medical condition, previous medical history, etc. In general, it is desirable to provide the recipient with a dosage of the above bacteria which is in the range of from about $10^5$ cfu/kg to $10^8$ cfu/kg (body weight of patient), although a lower or higher dosage may be administered.

In addition to the Gram-negative bacterium mutant, the invention can also include combination vaccines comprising a vaccine strain capable of inducing protection against another pathogen.

In a particular embodiment of the invention, the Gram-negative bacteria of the invention belong to the *Brucella* genus. In this embodiment, the invention relates to these Gram-negative bacteria for use in a method for treatment of brucellosis in the human or animal body. Indeed, the brucellae are facultative intracellular parasites that infect a variety of mammals and have a great impact in animal and human health worldwide. These gram-negative bacteria lack typical virulence factors and behave as stealthy parasites that avoid detection by innate immunity at the onset of infection, thus retarding an adaptive cellular response and making possible for this pathogen to reach sheltered intracellular niches. This ability is not related to an induction of regulatory cytokines such as IL-10 but rather to the failure of innate immunity pathogen-recognition receptors (PRRs) to identify the *Brucella* surface molecules that normally bear the cognate pathogen-associated molecular patterns (PAMP) (Barquero-Calvo E et al. (2007) PLoS ONE 2: e631), and in particular the LPS of these strains. The strains of the invention, which lack a particular portion of the core of the LPS, have been shown by the inventors to induce a strong immune response and are thus suitable for use as vaccine against brucellosis.

As described previously, in a particular embodiment, the invention also concerns Gram-negative bacteria lacking the branched structure of the core and partially or totally lacking the O-chain. These double mutant bacteria are useful for distinguishing animals that are vaccinated with said double mutant bacteria and animals that are infected with the wild type Gram-negative bacteria.

The invention thus concerns a method for determining Gram-negative bacteria infection in an animal comprising the step of examining a sample obtained from said animal for the presence or absence of antibodies reactive with the immunodominant epitopes (C, C/Y, A and M or combinations thereof) of the O-chain (Alton, G. G. et al. 1988, Techniques for the brucellosis laboratory—INRA, Paris, France; Gall, D. et al. 2004, Rev. Sci. Tech. 23:989-1002). The sample of the animal used in this method may be any sample in which said antibodies can be detected, e.g. a blood, serum or tissue sample.

The presence or the absence of antibodies can be detected by any immunoassay known by the person skilled in the art. The design of this immunoassay may vary. For example, the immunoassay may be based upon competition or direct reaction. Furthermore, protocols may use solid supports or may use cellular material. The detection of the antibody-antigen complex may involve the use of labeled antibodies; the labels may be, for example, enzymes, fluorescent, chemiluminescent, radioactive or dye molecules. Suitable methods for the detection of the above mentioned epitopes in the sample include, for example, the enzyme-linked immunosorbent assay (ELISA), immunofluorescent tests and Western blot analysis.

In another aspect, the invention concerns an isolated lipopolysaccharide obtainable from a gram-negative bacterium according to the invention. Indeed, the inventors have found that the modified LPS produced by the Gram-negative bacteria according to the invention stimulate an unspecific production of cytokines, in particular of IL 12 and TNFα, by dentritic cells (FIG. 6B) in the mouse.

The LPS can be extracted from the Gram-negative bacteria according to the invention following any method known by the skilled person, as for instance the method described in Garin-Bastuji B et al. (1990) J Clin Microbiol 28: 2169-2174; Leong D et al. (1970) Infection and Immunity 1: 174-182; and Velasco, J., J. A. Bengocchea, K. Brandenburg, B. Lindner, U. Seydel, D. Gonzalez, U. Zähringer, E. Moreno, and I. Moriyón. 2000. *Brucella abortus* and its closest phylogenetic relative, *Ochrobactrum* spp., differ in outer membrane permeability and cationic peptide resistance. Infect. Immun. 68:3210-3218.

As a result, in one embodiment, the modified LPS according to the invention can be used in a method for stimulating the immune system of the human or animal body.

In another embodiment, the invention concerns an adjuvant comprising a lipopolysaccharide according to the invention.

In addition, the invention concerns a vaccine comprising an antigen and an adjuvant wherein said adjuvant comprises a lipopolysaccharide according to the invention. According to this embodiment, the LPS according to the invention enhances the immune response induced by the antigen comprised in the vaccine.

In another embodiment of the invention, the LPS according to the invention is conjugated with a carrier molecule, in order to enhance its immunogenicity. The invention thus concerns a conjugate comprising a lipopolysaccharide obtainable from a gram-negative bacterium according to the invention linked to a carrier molecule. According to this embodiment, the LPS/carrier conjugate induces a specific immune response against the LPS and can thus be used as a vaccine. Non limitative examples of carrier molecules are carrier proteins, such as the tetanus toxoid or the diphtheria toxoid.

Further aspects and advantages of this invention will be disclosed in the following figures and examples, which should be regarded as illustrative and not limiting the scope of this application.

BRIEF DESCRIPTION OF THE FIGURES

FIG. 3: BABΔlpcC shows increased sensitivity to the killing action of normal serum that relates to the LPS defect. (A), survival of BAB-parented, BABΔlpcC, BABTn5::per and BABTn5::bvrR after incubation in non-immune serum for 90 min. Data are the media±standard error of three simultaneous measurements (the results shown are representative of three independent experiments); (B), gel to liquid crystalline (β⇌α) phase transition of the hydrocarbon chains of Ba wt-LPS and Ba LpcC-LPS in presence or absence of normal human serum. The position of the peak of the symmetric stretching vibration of the methylene groups vs(CH2) versus temperature is plotted.

EXAMPLES

Figure 1:
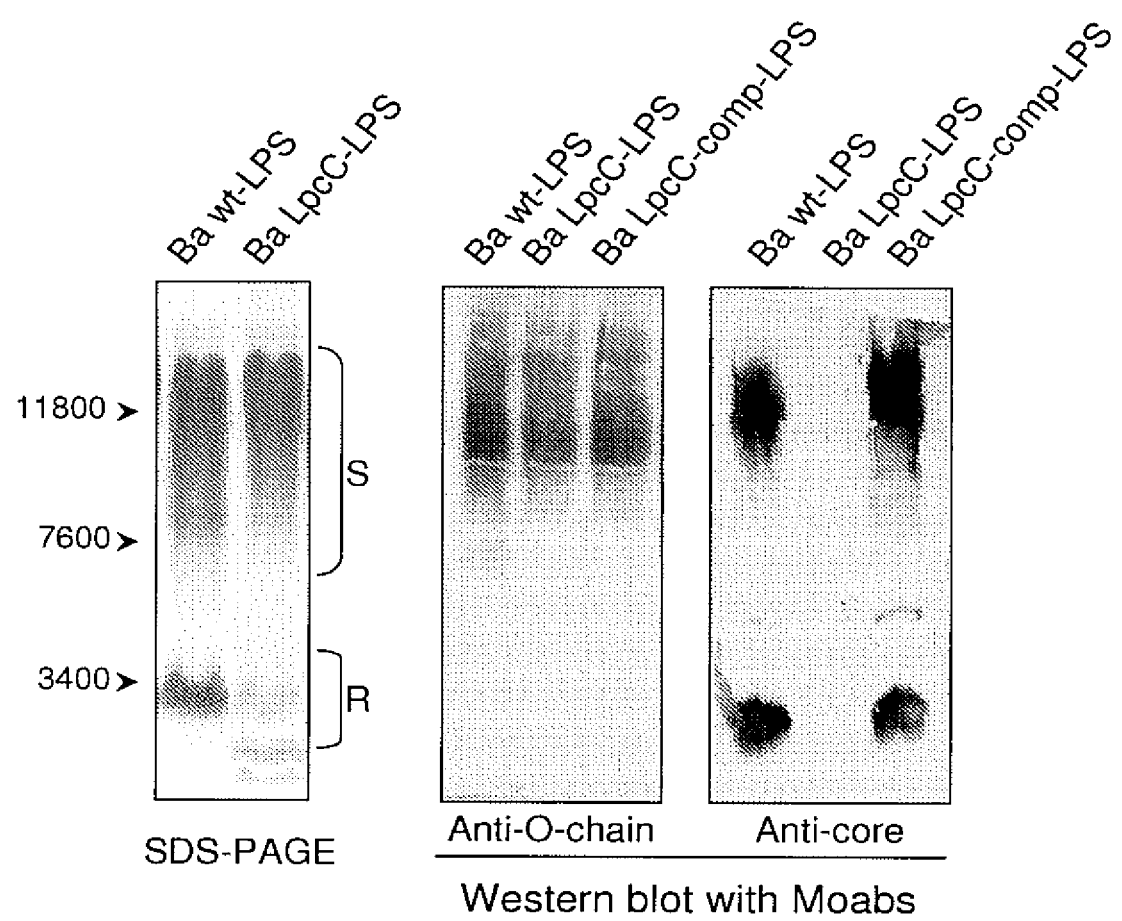
FIG. 1: The BABΔlpcC has a defect in the LPS core. SDS-PAGE of phenol-water extracts and Western blot analysis of LPS SDS-proteinase K extracts from BAB-parental (Ba wt-LPS), BABΔlpcC (Ba LpcC-LPS), and BABΔlpcCplpcC (Ba LpcC-compl-LPS) strains. The Moabs used were Cby-33H8 (to C/Y epitope of the O-chain) and A68/24D08/G09.

In the following description, all molecular biology experiments for which no detailed protocol is given are performed according to standard protocols.

Material and Methods

Bacterial Strains and Growth Conditions.

The bacterial strains and plasmids used are listed in Table 1:

TABLE 1

Bacterial strains and plasmids

| Strain/plasmids | Relevant characteristics | Reference/Source |
|---|---|---|
| *Brucella abortus* | | |
| B. abortus 2308 | Wild type, virulent, biotype 1, S-LPS. | |
| BAB-parental | Nal$^R$ spontaneous mutant of strain B. abortus 2308 | (Sangari and Agüero 1991) |
| BABΔlpcC | BAB-parental.lpcC$_{A16-308}$ | This work |
| BABΔlpcC-plpcC | BABΔlpcC harboring plasmid plpcC | This work |
| BABTn5::per | 2308 NalR per::Tn5; rough-LPS | (Monreal et al. 2003) |
| virB10::Gm | 2308 NalR Gm$^R$, nonpolar mutant of virB10 | (Sieira et al. 2000) |
| BAB-Tn5::bvrR | BAB-parental bvrR::Tn5, S-LPS; fully attenuated; sensitive to normal serum | Mutant 65.21 in Sola-Landa et al. 1998) |
| BAB-parental GFP | BAB-parental harboring pBBR1MCS-2 GFP Km$^R$ | This work |
| BABΔlpcC GFP | BABΔlpcC harboring pBBR1MCS-2 GFP Km$^R$ | This work |
| B. abortus S19 | | Dr. J.M. Blasco, C.I.T.A. Gobierno Aragón. |
| *E. coli* | | |
| S17-1 | Mating strain with plasmid RP4 inserted into the chromosome | (Simon et al. 1983) |
| Top10 F | F-Iaclq Tn 10 (Teir) mcrA Δ(mrr-hsdRMS-mcrBC) 80lacZΔM15 ΔlacX74 recA1alaD139 Δ (ara-leu)7697 galU galK rpsL endA1 nupG | Invitrogen |
| Plasmids | | |
| pCR2.1 | Cloning vector | Invitrogen |
| pJQK | Derivative of pJQ200KS +; Km$^R$; Gm$^S$ | (Scupham and Triplett 1997) |
| pRH001 | Derivative of pMR10 Km$^R$; Cm$^R$ | (Hallez et al. 2007) |
| pRCI-23 | 1019-bp of BAB-parental chromosomal DNA containing the lpcC deletion allele, generated by PCR and cloned into pCR2.1 | This work |
| pRCI-26 | BamHI-XbaI fragment from pRCLI-23 cloned into the corresponding sites of pJQK | This work |
| pDONR201 BMEl0509 | B. melitensis chromosomal DNA containing the complete lpcC gene, generated by PCR and cloned into pDONR201 (Invitrogen) | (Dricot et al. 2004) |
| plpcC | attL1-attL2 fragment of pDONR201-BMEl0509 cloned into the attR1-attR2 sites of pRH001 | This work |
| pBBR1MCS-2 GFP | pBBR1MCS-2 derivative expressing the gfp-mut3 gene under the control of the lack promoter | Dr. J.P, Garver, INSERM-CNRS, Marseille, France. |

Bacteria were routinely grown in standard tryptic soy broth or agar either plain or supplemented with kanamycin at 50 µg/ml, or/and nalidixic at 25 µg/ml, or/and 5% sucrose. All strains were stored in skim milk at −80° C.

LPS Extraction and Characterization.

Extraction of whole-cell LPS by SDS-proteinase K protocol was performed as described previously (Garin-Bastuji B et al., (1990) J Clin Microbial 28: 2169-2174). In addition, LPS was obtained by methanol precipitation of the phenol phase of a phenol-water extract (Leong D et al. (1970) Infection and Immunity 1: 174-182). This fraction (10 mg/mL in 175 mM NaCl, 0.05% NaN3, 0.1 M Tris-HCA [pH 7.0]) was then purified by digestion with nucleases (50 µg/ml each of DNase-II type V, and RNase-A [Sigma], 30 min at 37° C.) and three times with proteinase K (50 µg/ml, 3 hours at 55° C.), and ultracentrifuged (6 h, 100,000×g) (Aragon V et al. (1996) J Bacterial 178: 1070-1079). Free lipids (ornithine lipids and phospholipids) were then removed by a fourfold extraction with chloroform-methanol. (2:1 [vol/vol]) (Velasco 1 et al. (2000) Infect Immun 68: 3210-3218).

LPSs were analyzed in 15 or 18% polyacrylamide gels (37.5:1 acrylamide/methylene-bisacrylamide ratio) in Tris-HCl-glycine and stained by the periodate-alkaline silver method (Tsai C M et al. (1982) Anal Biochem 119: 115-119). For Western blots, gels were electrotransferred onto nitrocellulose sheets (Schleicher & Schuell GmbH, Dassel, Germany), blocked with 3% skim milk in 10 mM phosphate-buffered saline (PBS) with 0.05% Tween 20 overnight, and washed with PBS-0.05% Tween 20. Immune sera were diluted in this same buffer and, after incubation overnight at room temperature, the membranes were washed again. Bound immunoglobulins were detected with peroxidase-conjugated goat anti-mouse immunoglobulin (Nordic) and 4-chloro-1-naphthol-$H_2O_2$. Monoclonal antibodies (Moabs) used in this study were Cby-33H8 (Ingenasa, Madrid, Spain), which recognizes the C/Y O-chain epitope, and A68/24D08/G09, A68/24G12/A08, and A68/3F03/D5 which recognize core epitopes (Bowden R A et al. (1995) Infection and Immunity 63: 3945-3952). The inner core LPS marker 3-Deoxy-D-manno-2-octulosonic acid (Kdo) was determined calorimetrically by the thiobarbituric acid method using pure Kdo and deoxyribose as the standards, with the modifications described previously (Díaz-Aparicio E et al. (1993) J Clin Microbiol 31: 3136-3141; Díaz-Aparicio E et al. (1993) J Clin Microbiol 31: 3136-3141).

Determination of the Aggregate Size and Critical Aggregation Concentration of LPS.

The aggregate size of LPSs was determined by dynamic light scattering. Stock LPS suspensions were prepared at 1 mg/mL in deionized, reverse osmosis purified water and subjected to three cycles of heating to 56° C. and cooling to 4° C. to homogenize them. On the day of use, serial dilutions in the range 1 to 500 µg/mL were prepared and filtered through 0.45 µm, low protein binding Durapore® (PVDF) membranes immediately before measuring. Light scattering measurements were carried out in a DynaPro apparatus at 37° C. using a laser of 825 nm and 90° scattering angle. The data were analyzed by the regularization method in the Dynamics V6 software.

The critical aggregation concentration of LPS was determined by steady-state fluorescence using N-phenyl-1-naphthylamine (NPN), a hydrophobic fluorescent probe, whose quantum yield increases in hydrophobic environments. NPN (500 µM in acetone) was added into 1 mL of water to reach NPN at 15 µM final concentration in a quartz cuvette 1 cm optical. Then different volumes from a stock of LPS were added (from 1 µg/mL to 100 µg/mL, final concentration).

Fluorescence was measured (excitation, 350 nm; emission scan, 380 nm-600 nm) in Edinbugrh FLS920 apparatus at 37° C.

Determination of the Acyl-Chain Fluidity of LPS.

The transition of the acyl chains of LPS from a well-ordered state (gel phase) to a fluid state (liquid crystalline phase) at a lipid-specific temperature (Tc) was determined by Fourier transform infrared spectroscopy. A specific vibrational band, the symmetric stretching vibration of the methylene groups vs(CH2) around $2,850 \, cm^{-1}$, was analyzed since its peak position is a measure of the state of order (fluidity) of the acyl chains (Brandenburg K et al. (1997) Biochim Biophys Acta 1329: 183-201). Measurements were performed in a Bruker IFS 55 apparatus (Bruker, Karlsruhe, Germany) as described previously (Brandenburg K et al. (1997) Biochim Biophys Acta 1329: 183-201). To ensure homogeneity, LPS suspensions were prepared in 2.5 mM HEPES (pH 7.2) at room temperature, incubated at 56° C. for 15 min, stirred, and cooled to 4° C. This heating cooling step was repeated three times, and the suspensions were stored at 4° C. for several hours before analysis. LPS suspensions (water content, 90%) were analyzed in $CaF_2$ cuvettes with 12.5-µm Teflon spacers, and for each measurement, 50 interferograms were accumulated, Fourier transformed, and converted to absorbance spectra. The measurements were obtained in continuous heating scans (2° C./min) between 10° C. and 60° C. To test the effect of complement, the experiments were performed in the presence of normal human serum. The effect of polymyxin B was assessed similarly at different LPS:polymyxin B molar ratios (see Results), and using an average MW of 11800 for *B. abortus* LPS (determined by SDS-PAGE with *Yersinia enterocolitica* O:8 LPS as a standard).

DNA Manipulations.

Plasmid and chromosomal DNA were extracted with Qiaprep spin Miniprep (Qiagen GmbH, Hilden, Germany), and Ultraclean Microbial DNA Isolation kit (Mo Bio Laboratories) respectively. When needed, DNA was purified from agarose gels using Qiack Gel extraction kit (Qiagen). DNA sequencing was performed by the Servicio de SecuenciaciOn de CIMA (Centro de Investigación Médica Aplicada, Pamplona, Spain). Primers were synthesized by Sigma-Genosys Ltd. (Haverhill, United Kingdom). Searches for DNA and protein homologies were carried out using the NCBI (http://www.ncbi.nlm.nih.gov) and the EMBL-European Bioinformatics Institute server (http://www.ebi.ac.UK/ebi_home.html). In addition, sequence data were obtained from The Institute for Genomic Research website at http://www.tigr.org. Genomic sequences of *B. melitensis* 16M, *B. abortus* and *B. suis* were analyzed using the database of the URBM bioinformatic group (http://www.serine.urbm.fundp.ac.be/~seqbruce/GENOMES/Brucella_melitensis).

Construction of the *B. abortus* lpcC Non Polar Mutant (BABΔlpcC).

In-frame deletion mutant BABΔlpcC was constructed by PCR overlap using genomic DNA of *B. abortus* 2308 as DNA template. Primers were designed based on the available sequence of the corresponding genes in *B. abortus* 2308. For the construction of the lpcC mutant, we first generated two PCR fragments: oligonucleotides lpcC-F1 (5'-CTGGCGT-CAGCAATCAGAG-3'; SEQ ID NO:17) and lpcC-R2 (5'-GTGCAACGACCTCAACTTCC-3'; SEQ ID NO:18) were used to amplified a 476-bp fragment including codons 1 to 16 of the lpcC ORF, as well as 424 bp upstream of the lpcC start codon, and oligonucleotides lpcC-F3 (5'-GGAAGTTGAG-GTCGTTGCACACGCCATCGAACCTTATCTG-3'; SEQ ID NO:19) and lpcC-R4 (5'-CGGCTATCGTGCGATTCT-3'; SEQ ID NO:20) were used to amplify a 453-bp fragment including codons 308 to 354 of the lpcC ORF and 320-bp downstream of the lpcC stop codon. Both fragments were ligated by overlapping PCR using oligonucleotides lpcC-F1 and lpcC-R4 for amplification, and the complementary regions between lpcC-R2 and lpcC-F3 for overlapping. The resulting fragment, containing the lpcC deletion allele, was cloned into pCR2.1 (Invitrogen), to generate plasmid pRC1-23, sequenced to ensure the maintenance of the reading frame, and subsequently subcloned into the BamHI and the XbaI sites of the suicide plasmid pJQK (Scupham A J et al. (1997) Gene 202: 53-59). The resulting mutator plasmid (pRCI-26) was introduced in *B. abortus* 2308 bp conjugation. The first recombination (integration of the suicide vector in the chromosome) was selected by Nal and Kan resistance, and the second recombination (excision of the mutator plasmid leading to construction of the mutant by allelic exchange), was selected by Nal and sucrose resistance and Kan sensitivity. The resulting colonies were screened by PCR with primers lpcC-F1 and lpcC-R4 which amplify a fragment of 929 bp in the mutant and a fragment of 1805 bp in the parental strain. The mutation generated results in the loss of the 82% of the lpcC ORF, and the mutant strain was called BABΔlpcC.

Complementation of BABΔlpcC.

Taking into account that the LpcC sequences of *B. melitensis* and *B. abortus* are identical, we used the *B. melitensis* ORFeome constructed with the Gateway cloning Technology (Invitrogen) for complementation (Dricot A et al. (2004) Genome Res 14: 2201-2206). The clone carrying *B. melitensis* lpcC was extracted, and the DNA containing the corresponding ORF was subcloned in pRH001 (Hailez R et al. (2007) Appl Environ Microbiol 73: 1375-1379) to produce plasmid plpcC. To complement the lpcC mutation, plasmid plpcC was introduced into the BABΔlpcC mutant by mating with *E. coli* S17-1 and the conjugants harbouring piper (designated as BABΔlpcCplpcC) were selected by plating the mating mixture onto TSA-Nal-Kan plates which were incubated at 37° C. for 3 days.

Sensitivity to Brucellaphages, Dyes, Antibiotics and Polycationic Bactericidal Peptides The minimal inhibitory concentrations (MICs) of polymyxin B, poly-L-ornithine, poly-L-lysine, colistin, penicillin, doxycycline, clarithromycin, erythromycin, rifampicin, basic fuchsin, safranin and thionine was determined in Müller-Hinton medium by standard procedures. Sensitivity to the S (Wb, Iz) and rough (R/C)-specific brucellaphages was measured by testing the lysis of bacteria exposed to serial 10-fold dilutions made from a routine test dilution phage stock (Alton G G et al. (1988) Techniques for the brucellosis laboratory. Paris, France: INRA).

Sensitivity to the Bactericidal Action of Nonimmune Serum.

Exponentially growing bacteria were adjusted to $10^4$ CFU/ml in saline and dispensed in triplicate in microtiter plates (45 µl per well) containing fresh normal bovine serum (90 µl/well). After 90 min of incubation at 37° C., brain heart infusion broth was dispensed (200 µl/well), mixed with the bacterial suspension and 100 µl was plated on tryptic soy agar. Results were expressed as the percentage of the average CFU with respect to the inoculum.

Intracellular Multiplication.

Bone marrow cells were isolated from femurs of 7-8-week-old C57Bl/6 female, TLR4/ (Hoshino K et al. (1999) J Immunol 162: 3749-3752) or TLR9-/- (Hemmi H et al. (2000) Nature 408: 740-745) mice and differentiated into either dendritic cells (BMDCs) or macrophages (BMDM) as described by Inaba et al. or De Chastellier et at (Inaba K et al. (1992) J Exp Med 176: 1693-1702; Inaba K et al. (1992) J Exp Med 176: 1693-1702; De Chastellier C et al. (1993) Infect Immun 61: 3775-3784), respectively. Infections were performed by centrifuging the bacteria onto the differentiated cells (400×g for 10 min at 4°; bacteria: cells ratio of 20:1 for BMDCs or 50:1 for BMDM) followed by incubation at 37° C. for either 15 min (BMDM) or 30 min (BMDCs) under a 5% $CO_2$ atmosphere. Cells were either extensively washed (BMDM) or gently washed (BMDCs) with medium to remove extracellular bacteria and incubated in medium supplemented with 100 µg/ml gentamycin for 1 h to kill extracellular bacteria. Thereafter, the antibiotic concentration was decreased to 20 µg/ml. To monitor *Brucella* intracellular survival, infected cells were lysed with 0.1% (vol/vol) Triton X-100 in H2O (BMDCs) or after PBS washing (BMDM) and serial dilutions of lysates were rapidly plated onto tryptic soy agar plates to enumerate CFUs.

Immunofluorescence Assays.

BMDCs were grown on glass coverslips and inoculated with bacteria as described above. At different times after inoculation (see Results), coverslips were fixed with 3% paraformaldehyde pH 7.4 at 37° C. for 15 min and washed three times with PBS. Coverslips were processed for immunofluorescence staining as previously described (Celli J et al. (2003) J Exp Med 198: 545-556). Briefly, cells were permeabilized with 0.1% saponin and incubated with primary antibodies. After several washes, the primary antibodies were revealed with the appropriate secondary antibodies. The primary antibodies used for immunofluorescence microscopy were: cow anti-*B. abortus*; rat anti-mouse LAMP 1 ID4B (Developmental Studies Hybridoma Bank, National Institute of Child Health and Human Development, University of Iowa); mouse anti FK2 (Biomol) and Moab anti-calnexin (kindly provided by Dr. D. Williams, University of Toronto). In all experiments, BMDCs were labeled using an antibody against a conserved cytoplasmic epitope found on MHC-II 1-A β subunits (Lelouard H et al. (2002) Nature 417: 177-182) which does not produce significant labeling with BMDM and were also labeled with an anti-CD11c antibody (Biolegend) confirming that they are DCs (Salcedo S P et al. (2008) PLoS Pathogens 4: e21). Samples were analyzed under a Leica DMRBE epifluorescence microscope for quantitative analysis, or a Zeiss LSM 510 laser scanning confocal microscope for image acquisition.

Cytokine Measurement.

Sandwich enzyme-linked immunosorbent assays (ELISA) (AbCys, Paris, France) were used to detect IL-12 (p40/p70) and TNFα in the supernatants of BMDCs 24 hours after infection (see above) or after stimulation with 10 µg/ml of the appropriate LPS from different *Brucella* strains or 100 ng/ml from *E. coli* ATCC 35218 obtained by the phenol-water procedure and purified further by the phenol-water-deoxycholate method. For the latter purpose, a stock of 1 mg/ml in pyrogen free sterile water was prepared, sonicated briefly and sterilized by autoclaving. Prior to use, the stock was heated at 56° C. for 15 min and then cooled to room temperature.

LPS Binding to hMD-2 by Competitive ELISA.

The ELISA for determination of LPS binding to hMD-2 was performed in 96-well plates (NUNC immunoplate F96 cert. Maxi-sorp). Chicken anti-hMD2 (GenTel) (5 µg/mL) in 50 mM $Na_2CO_3$ (pH 9.6) was used to coat the microtiter plate at 4° C. overnight. Excess binding sites were blocked with 1% BSA in 10 mM PBS buffer (pH 7.2) for 1 h at room temperature, and rinsed three times with the same buffer. During the blocking step, hMD-2 (0.75 µM) was preincubated with 0 µM to 8 µM LPS at 37° C. and, as a negative control, LPS was also preincubated in absence of hMD2. This preincubated solutions were added to the plate, which was then incubated for 1 h at 37° C. After rinsing, hMD-2 not bound to LPS was detected by incubation with 0.1 µg/ml of mouse anti h-MD2 (clone 9B4 e-Bioscience) in 10 mM PBS buffer at 37° C. for 1 h, followed by incubation with 0.1 µg/ml peroxidase-conjugated goat anti-mouse IgG (Santa Cruz), also in PBS buffer at 37° C. for 1 h. After plate washing, ABTS (Sigma) was added, the reaction was stopped with 1% SDS after 15 min, and the absorbance at 420 nm measured using a Mithras LB940 apparatus. (Berthold Technologies).

Virulence Assay in Mice.

Infection experiments were performed as described in Conde-Alvarez, R. et al., 2006, Cell. Microbiol. 8:1322-1335. For each strain, 30 mice were inoculated intraperitoneally with 0.1 mL of inoculum containing $5.8 \times 10^4$ (parental control) and $4.9 \times 10^4$ (BABΔlpcC) CFU/mouse and the number of CFU in spleens (n=5) was determined at 1, 2, 4, 6, 8, and 12 weeks after inoculation. The identity of the spleen isolates was confirmed by PCR at several points during the infection process. The individual data were normalized by logarithmic transformation, and the mean and standard deviation of log CFU/spleen were calculated. Statistical comparisons were performed by the Fisher's Protected Least Significant Differences test. An additional infection was performed under the same conditions but including BABΔlpcC harboring plpcC. The number of CFU in spleens was determined 8 weeks after inoculation.

Protection Studies in Mice.

Three groups of 10 mice each were inoculated subcutaneously with $3.9 \times 10^4$ CFU of BABΔlpcC, $1.3 \times 10^5$ of *B. abortus* S19 per mouse, or sterile saline as a control. Four weeks after vaccination, each group was challenged by intraperitoneal injection of $3.6 \times 10^4$ CFU of virulent *B. abortus* per mouse. To differentiate the challenge from the vaccine strain, BAB-parental GFP (Table 1) was used taking advantage of its kanamycin resistance (in preliminary experiments, the virulence of BAB-parental GFP was measured and found to be identical to that of BAB-parental). Two and six weeks later, mice were euthanized by cervical dislocation, and the CFU of the challenge strain in the spleens was determined on tryptic soy agar supplemented with kanamycin (see above). The mean±SD of the log CFU per spleen was calculated and statistical comparisons made as described above. The vaccine and challenge doses, routes, and challenge intervals were chosen on the basis of previous evidence (Grillo M J et al. (2000) Biologicals 28: 119-127; Stevens M G et al, (1995) Infection and Immunity 63: 264-270).

Results

Construction and Characteristics of a *B. abortus* lpcC Mutant.

To analyze the role of ORF BAB1_1522 in the synthesis of *Brucella* LPS, we constructed a non-polar mutant (BAB-ΔlpcC) by making an in frame internal deletion of the region coding for amino acids 17 to 307. To test if the mutation induced cell envelope modifications or changes in the permeability pattern characteristic of *Brucella* (Martinez de Tejada G et al. (1993) J Bacteriol 175: 5273-5275), we compared the sensitivity of the BAB-parental strain and the BABΔlpcC mutant to S and R brucellaphages, dyes (fuchsin, thionine and safranine) and hydrophobic (erythromycin, rifampicin) and hydrophilic (penicillin, doxycycline, clarithromycin) antibiotics. Both strains behaved similarly in all tests performed and, moreover, showed similar growth rates (data not shown).
the BABΔlpcC Mutant has a Defect in the LPS Core.

Figure 2:
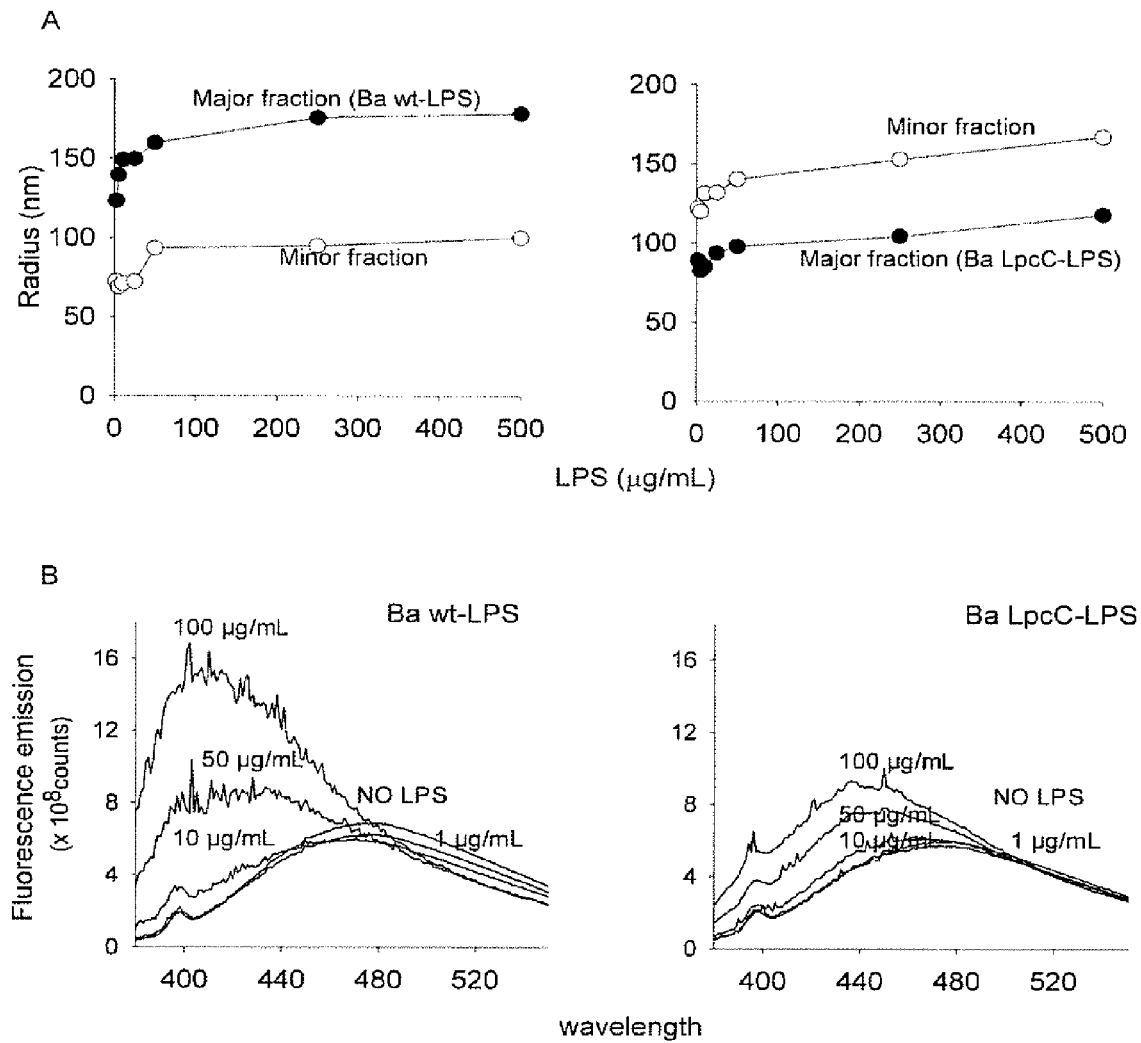
FIG. 2: Aggregate state of Ba wt-LPS and Ba LpcC-LPS. (A), aggregate size of the major and minor LPS fractions on dependence of concentration measured by light scattering. (B), determination of the critical aggregate concentration by fluorescence emission of NPN (the increase in fluorescence caused by the partition of NPN into the aggregates starts at 10 μg/mL for both Ba wt-LPS and Ba LpcC-LPS). Same values were obtained for minor fractions.

To analyze the effect of the lpcC mutation in the LPS structure, we extracted this molecule using the protocol developed for *Brucella* S-LPS (Leong D et al. (1970) Infection and Immunity 1: 174-182). This protocol includes a phenol-water partition followed by first digestion with nucleases and proteinase K and then ultracentrifugation, a step that allows the recovery of over 70% of the purified LPS in the sediment. Then, the LPS is freed from phospholipids and ornithine lipids by solvent extraction. However, when this method was applied to BABΔlpcC, the yield was only a 32% of that obtained with the parental strain, a result that could be due to either a diminished amount of LPS in BAB-ΔlpcC, or to a failure of the standard protocol to yield the LPS quantitatively. The first possibility was ruled out by measuring the whole bacterial LPS content using the SDS-proteinase K extraction method followed by Western blot with anti-O-chain Moab Cby-33H8 (C/Y specificity) (FIG. 1). When we reexamined the classical protocol, we found that the supernatant of the ultracentrifugation contained an unexpected amount of a material. By SDS-PAGE and Kdo analysis this material was similar to the S-LPS obtained in smaller amounts in the sediment of the ultracentrifugation step (not shown). These results suggested a different aggregation state in the parental and the BABΔlpcC S-LPSs, a possibility tested by measuring the aggregate size by dynamic light scattering. Both for the parental and BABΔlpcC S-LPSs, the aggregates in the supernatant fractions had an average ratio of ca. 100 nm whereas those in the sediment were of ca. 150 nm at concentrations above 100 μg/mL (FIG. 2). This, however, did not relate to a difference in the critical aggregate concentration of these LPSs (10 μg/ml), as shown by fluorimetry (FIG. 2). These results showed that the major fractions of the LPS of BABΔlpcC and BAB-parental differed in aggregate size.

The SDS-PAGE and Western-blot analysis showed that, as expected, the parental strain contained a wild type LPS consisting of both S and R fractions (FIG. 1). However, although there was no change in the total S-LPS content, the BAB-ΔlpcC LPS extracts had less amounts of R-LPS and with a different migration pattern from. This peculiarity, which was observed both in the supernatant (not shown) and the sediment fractions (FIG. 1), was corroborated by the lack of reactivity of the anti-core Moabs (FIG. 1) with LPS obtained from BABΔlpcC by the SDS-proteinase K procedure. Furthermore, when plasmid plpcC (encoding the lpcC gene) was introduced into BABΔlpcC the Moab reactivity was restored (FIG. 1). These results indicate that LpcC is required for the normal synthesis of the core LPS but not for the assembly and incorporation of the O-chain. Unless stated otherwise, the studies described below were performed with the major fractions of each bacteria (henceforth referred to as Ba wt-LPS and Ba LpcC-LPS).

An Intact LPS Core is Required for the Resistance of *B. abortus* to the Bactericidal Action of Polycationic Peptides and Normal Serum.

*S. brucellae* are resistant to the bactericidal action of normal serum, and this resistance has been attributed to the O-chain (Eisenschenk F C et al. (1999) Vet Microbiol 68: 235-244). However, some *B. melitensis* R mutants and *B. ovis* (a naturally R *Brucella* species) have been reported to be resistant to serum (David Gonzalez, Caro-Henandez, Fernandez-Prada), suggesting that the LPS core may also be important. To assess this possibility, BABΔlpcC, BABTn::5per, BABTn::5bvrR (Table 1) and BAB parental were incubated in normal serum for 90 minutes and tested for viability. As it can be seen in FIG. 3, BABΔlpcC was more sensitive than BAB-parental strain but not as much as bvrR mutant. Moreover, comparison with BABTn::5 per showed that the core was as important as the O-chain in this property.

Figure 3:
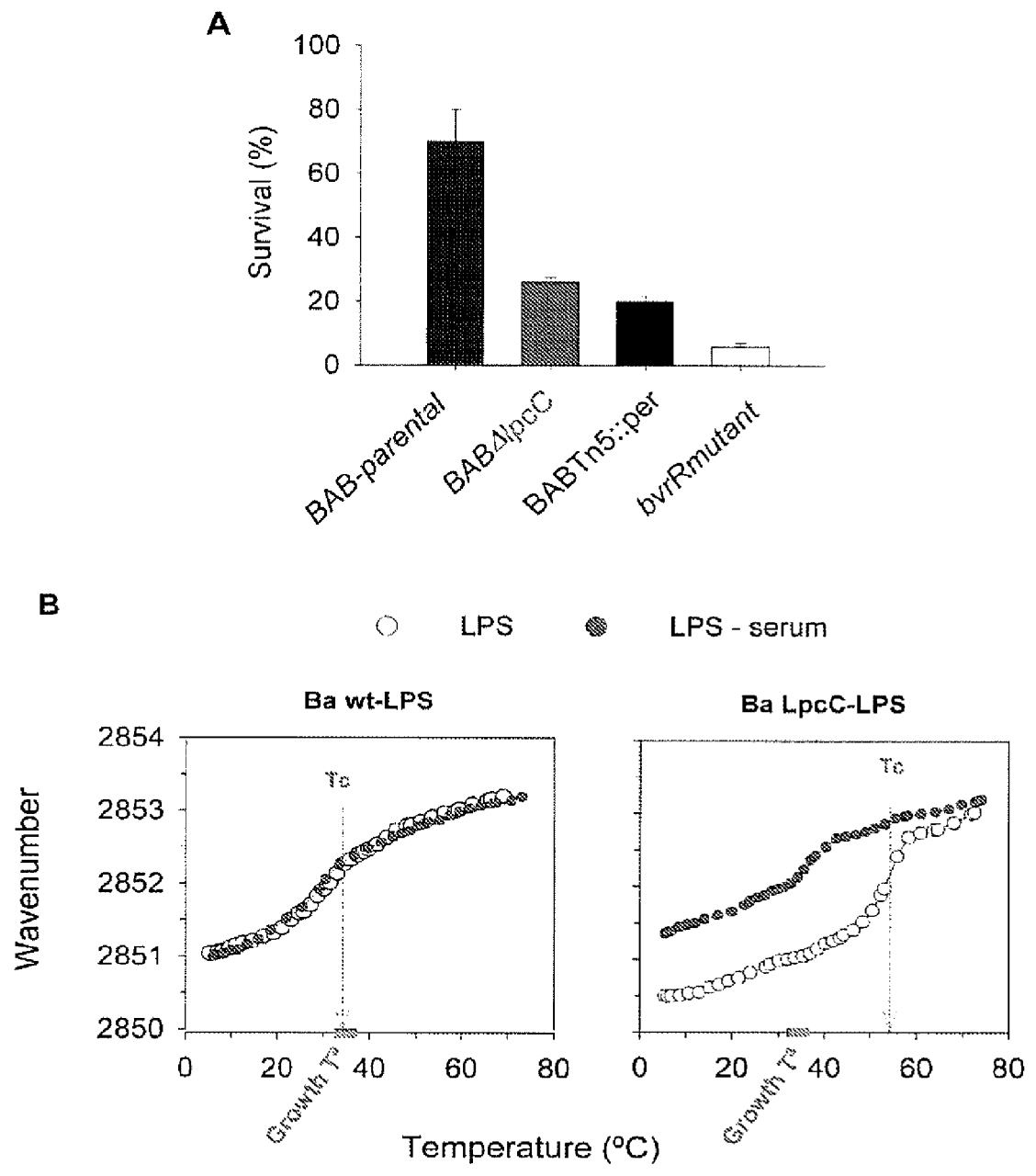

The involvement of the defect in the Ba LpcC-LPS in the increased serum sensitivity of BABΔlpcC was tested. To this end, we examined the lipid A acyl chain fluidity of Ba wt-LPS and Ba LpcC-LPS in the presence of serum, since this parameter increases upon binding of molecules to the LPS aggregates (Brandenburg K et al. (2005) Biophys J 88: 1845-1858). As it is shown in FIG. 3, the β⇌α transition that marks the shift from the crystalline to the fluid phase took place in the 30 to 40° C. range for the Ba wt-LPS, with a Tc of 37° C. in the absence of serum. Surprisingly, the Ba LpcC-LPS showed a very different fluidity profile with a Tc between 45 and 55° C., and with a more restricted acyl chain fluidity below Tc than the Ba wt-LPS, showing that the aggregates were in the crystalline phase at physiological temperatures. Despite this greater rigidity, Ba LpcC-LPS aggregates were clearly affected by the presence of normal serum whereas those of Ba wt-LPS were not (FIG. 3). These results suggest that the lack of part of the core could be uncovering complement targets and are in agreement with the serum sensitivity of the bacteria.

Figure 4:
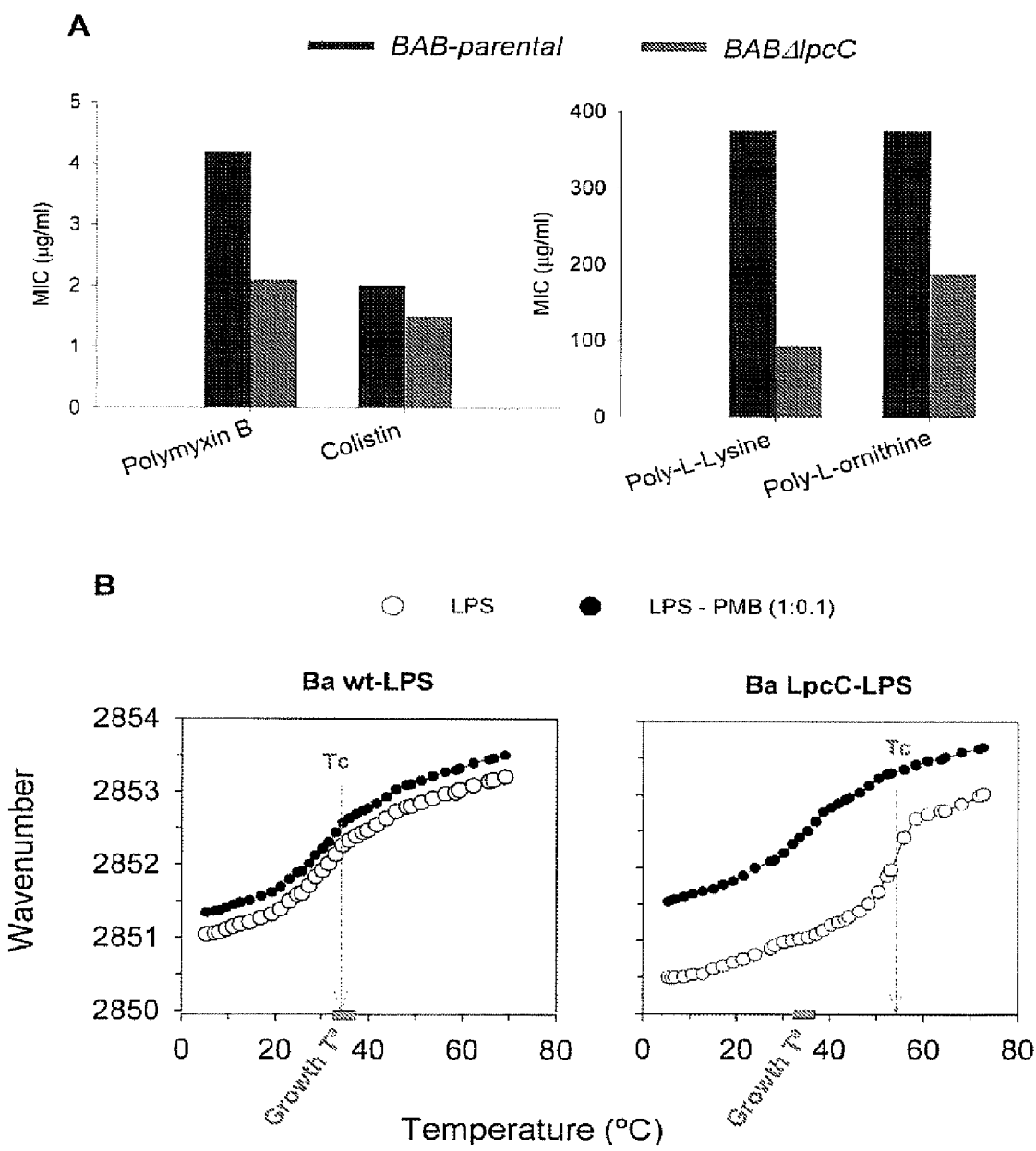
FIG. 4: BABΔlpcC shows increased sensitivity to polycationic bactericidal peptides that relates to the LPS defect. (A), MICs determined by the E-test (colistin) or serial dilution method (polymyxin B, poly-L-ornithine, poly-L-lysine). The results shown are representative of three experiments in which of BAB-parental, BABΔlpcC where assayed simultaneously; (B), gel to liquid crystalline (β⇌α) phase transition of the hydrocarbon chains of Ba wt-LPS and Ba LpcC-LPS in presence or absence of polymyxin B at a LPS:PMB 1:0.1 molar ratio. The position of the peak of the symmetric stretching vibration of the methylene groups vs(CH2) versus temperature is plotted.

*Brucella* is also resistant to bactericidal polycationic peptides (Martinez de Tejada G et al. (1995) Infect Immun 63: 3054-3061; Freer E et al. (1996) J Bacteriol 178: 5867-5876), a property linked mostly to the low negative charge in the core and lipid A LPS sections (Velasco J et al. (2000) Infect Immun 68: 3210-3218). To assess weather the core defect in BAB-ΔlpcC affected this property, we examined the sensitivity to polymyxin B, colistin, poly-L-lysine, and poly-L-ornithine. The results demonstrated a greater sensitivity of BABΔlpcC to all these agents (FIG. 4). Like in the serum sensitivity experiments, the Ba LpcC-LPS was tested for polycation binding by measuring acyl chain fluidity. FIG. 4 shows that polymyxin B increased the fluidity of Ba LpcC-LPS.

An Intact LPS Core is Required for *B. abortus* to Evade Lysosome Fusion and to Multiply in Dendritic Cells.

Figure 5:
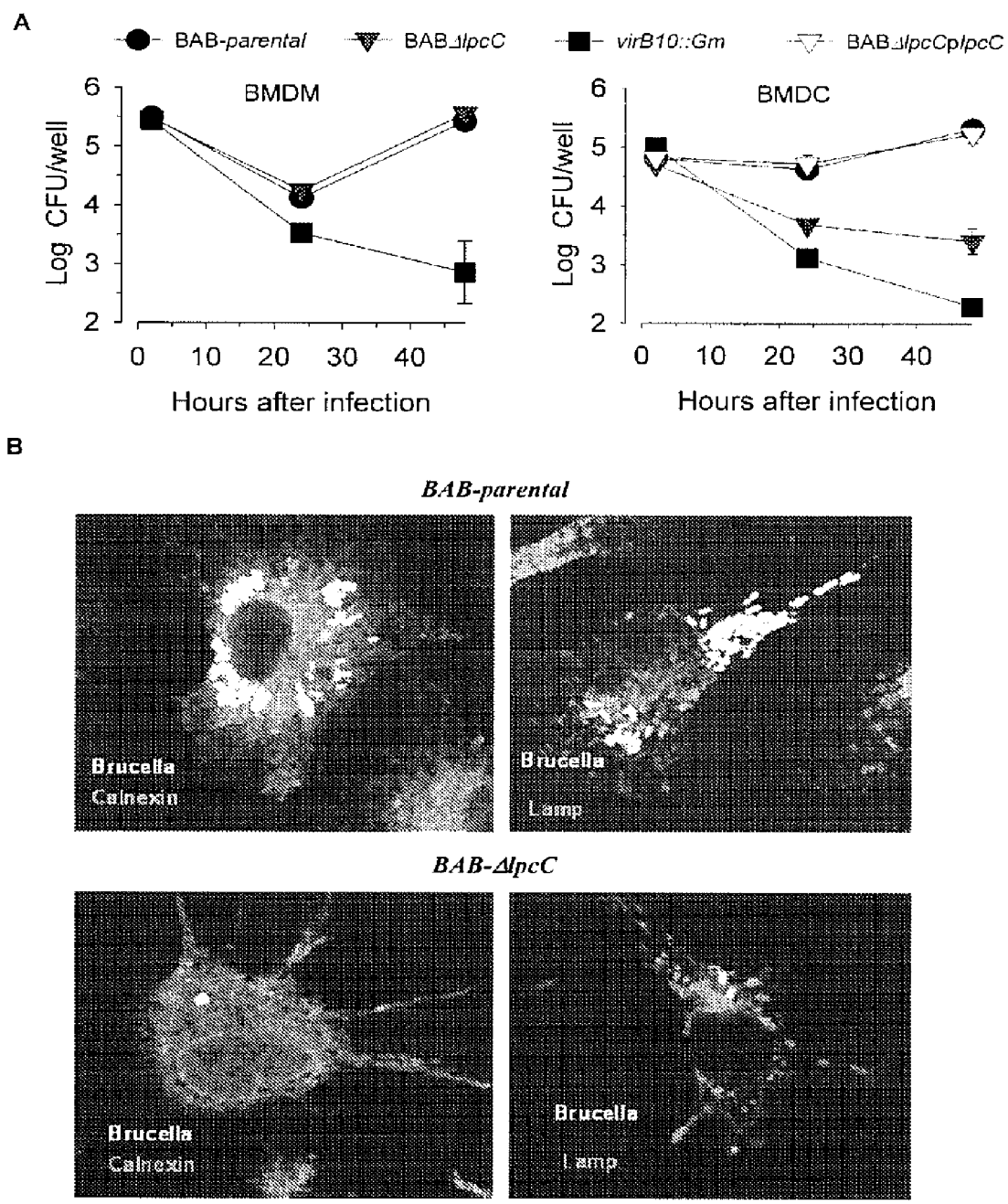
FIG. 5: BABΔlpcC is attenuated in dendritic cells but not in macrophages. (A), Kinetics of intracellular survival and replication of BAB parental, BABΔlpcC and BABΔlpcC-plpcC in BMDM (left panel) or BMDC (right panel) (a virB10::Gm mutant attenuated in both types of cells is included as a reference; each point represents the mean±standard error of triplicate wells of one representative experiment [three independent experiments were performed]); (B), confocal images of BMDCs infected with BAB parental GFP or BABΔlpcC GFP (clear grey) labeled with Moabs to either calnexin, or LAMP 1 (both in dark grey) 24 hours after infection.

BABΔlpcC was tested for their ability to multiply in bone marrow derived macrophages (BMDM) and dendritic cells (BMDCs) in comparison with BAB parental. The behavior in BMDM of both bacteria was similar thus showing no attenuation of the mutant in these cells (FIG. 5). In contrast, the attenuated virB mutant used as a control failed to multiply. In BMDCs, however, BABΔlpcC and BAB-parental showed a different behavior. Whereas BAB-parental was not destroyed and was able to multiply, BABΔlpcC decreased markedly either immediately after infection (FIG. 5A) or after 24 hours (not shown), depending upon the experiment, although not to the extent of the virB control. Complementation of BAB-ΔlpcC with plasmid plpcC restored the ability to multiply in these cells.

The intracellular location in BMDC was determined by confocal microscopy (FIG. 5B). Twenty-four hours after infection, BAB-parental was present in high number in BMDC whereas cells infected with BABΔlpcC were almost free of them. Moreover, the majority of BAB-parental bacteria colocalized with the endoplasmic reticulum marker calnexin, but not with the lysosomal marker LAMP-1. By contrast, the BABΔlpcC mutant was in LAMP1-positive vacuoles, apparently unable to establish an endoplasmic reticulum-derived compartment. Taken together, these results indicate that a higher proportion of mutant bacteria were degraded soon after uptake, showing that the LPS core has a role in the resistance of *B. abortus* to killing by dendritic cells. The LPS Core Deficiency Increases TNFα and IL12 Secretion by *B. abortus* Infected Dendritic Cells.

Figure 6:
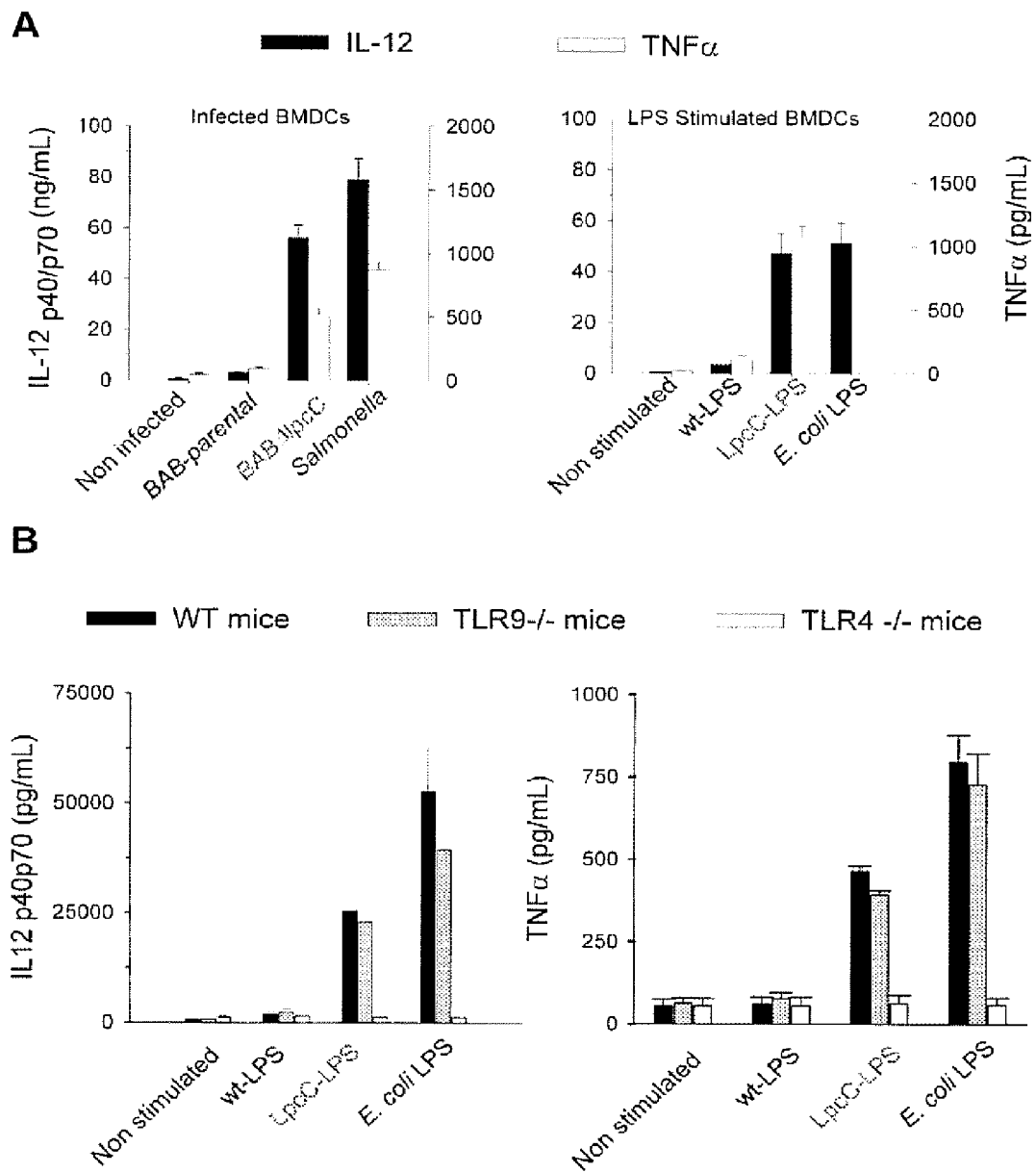
FIG. 6: BABΔlpcC stimulates a comparatively increased cytokine release in infected BMDC that is paralleled by the TLR4-dependent activity of the Ba LpcC-LPS. (A), cytokine levels in the supernatants (24 h incubation) of infected (left panel) of LPS stimulated (right panel) BMDC obtained from TLR wild type mice; (B), cytokine levels in the supernatants (24 h incubation) of LPS stimulated BMDC obtained from TLR ko mice. Codes for the bacteria and LPSs are those used in the text. Values correspond to mean±standard error of at least three independent experiments.

*Brucella* infection is characterized by a low induction of proinflammatory and inflammatory mediators, including TNFα, IL1beta, IL-6, IL-10, and IL-12, and LPS is a key molecule in this low recognition by innate immunity (Barquero-Calvo E et al. (2007) PLoS ONE 2: e631). Therefore, it was of interest to study the production of TNFα and IL-12 by BMDCs infected with BAB-parental and with BABΔlpcC and to see if the results were reproduced by stimulation with the LPSs. The results showed the mutant induced a stronger production of both cytokines which was paralleled by the Ba LpcC-LPS ability to stimulate secretion of both cytokines (FIG. 6). Furthermore, experiments in BMDCs obtained from the appropriate TLR mutants demonstrated that the effects were TLR4-dependent and, therefore, directly attributable to the LPS (FIG. 6). In addition, we observed that the minor LPS fraction in the supernatants of the BAB-parental extracts yielded similar results to those obtained with the Ba wt-LPS, but the sediment fraction corresponding to Ba LpcC-LPS failed to stimulate high amounts of either cytokine (not shown).

The LPS Core of *B. abortus* Modulates Recognition by MD2.

Figure 7:
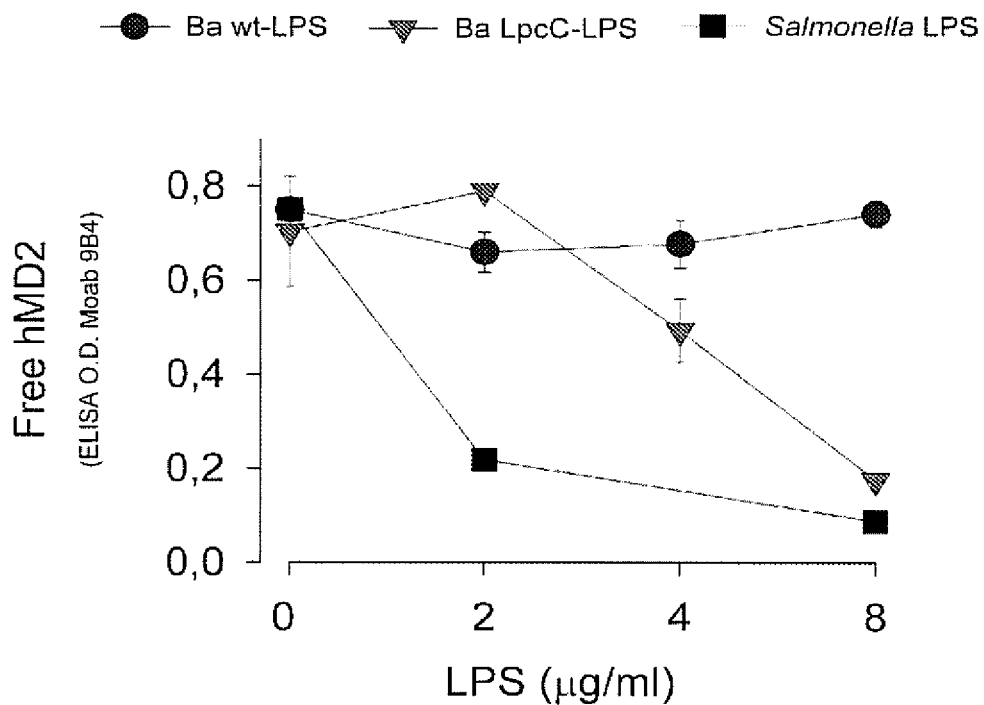
FIG. 7: Ba LpcC-LPS shows a comparatively increased binding to h-MD2.

Bacteria carrying a classical LPSs are recognized by the CD-14-MD2 TLR4 system which triggers a cascade of signals leading to cytokine production. In this recognition, MD2 plays a critical role and there is evidence that it interacts with classical LPSs through the core and lipid A section (Gruber A et al. (2004) J Biol Chem 279: 28475-28482; Ohto U et al. (2007) Science 316: 1632-1634). However, it is known that TLR4 mutations do not affect the course of *Brucella* infections (Barquero-Calvo E et al. (2007) PLoS ONE 2: e631; Lapaque N et al. (2006) Cellular Microbiology 8: 401-413) and that *Brucella* LPS weakly activates the TLR4-MD2 system (Dueñas A I, et al. (2004) Int Immunol 16: 1467-1475). Since BABΔlpcC induced anomalously high levels of cytokines as compared to BAB-parental, it was of interest to study the interaction of Ba LpcC-LPS with MD2. For this purpose, a competitive ELISA with hMD-2 and an antibody recognizing free hMD2 but not to LPS bound hMD2 was used (Gradisar H et al. (2007) J Leukoc Biol 82: 968-974; Gradisar H et al. (2007) J Leukoc Biol 82: 968-974). In agreement with the low cytokine induction in vivo, Ba wt-LPS did not inhibit antibody binding to hMD2 at any of the concentrations tested. In contrast, Ba LpcC-LPS inhibited binding at 40 μg/mL or higher concentrations, a value that, although clearly different from that of *S. enteritidis* LPS, departed from that of the Ba wt-LPS (FIG. 7). In this case, the minor fractions of the LPS extracts of both BAB-parental and BABΔlpcC reproduced these results, although not so patently for the latter. These results demonstrate that the LPS core of *B. abortus* contributes to the low recognition of *Brucella* LPS by MD2.

Inhibition of Dendritic Cell Maturation by *B. abortus* Requires and Intact LPS Core.

Figure 8:
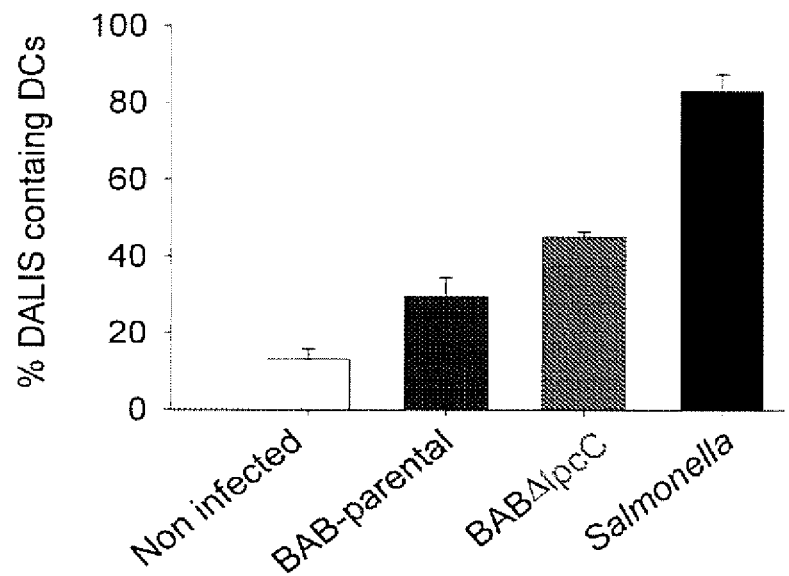
FIG. 8: BABΔlpcC stimulates a dendritic cell maturation. The figure shows the percentages of BMDCS infected with either BAB-parental, BABΔlpcC or *S. typhimurium* that contain DALIS.

In response to microbial products, dendritic cells undergo a maturation process that includes the formation of large polyubiquitinated protein aggregates, named dendritic cell aggresome-like induced structures (DALIS). DALIS are thought to contain misfolded proteins and components of the ubiquitin system, suggesting that ubiquitination of misfolded proteins occurs in these structures. It has been suggested that the storage of misfolded self proteins during infection may allow for efficient presentation of peptides from foreign microbial proteins. *Brucella* interferes with the maturation of dendritic cells, an ability that should favor the establishment of the infection (Salcedo S P et al. (2008) PLoS Pathogens 4: e21). To analyze whether the attenuation of BABΔlpcC in BMDC was accompanied by a defect in this interference, the formation of DALIS was examined using a FK2 Moab which recognizes ubiquitinated proteins (Fujimuro M (1994) FEBS Lett 349: 173-180). As it can be seen in FIG. 8, the BABΔlpcC mutant induced a higher number of DALIS than the parental strain. To relate this effect to the structure of Ba LpcC-LPS, we stimulated BMDC obtained from wild type, TLR4 or TLR9 (as a control) ko mice (data not shown). For the Ba wt-LPS, DALIS were not observed in any kind of dendritic cells. In contrast, Ba LpcC-LPS induced DALIS formation in and TLR9 ko but not in TLR4 ko cells, thereby demonstrating the involvement of the Ba LpcC-LPS in the induction of dendritic cell maturation.

An Intact LPS Core is Required for *B. abortus* Virulence in Mice.

Figure 9:
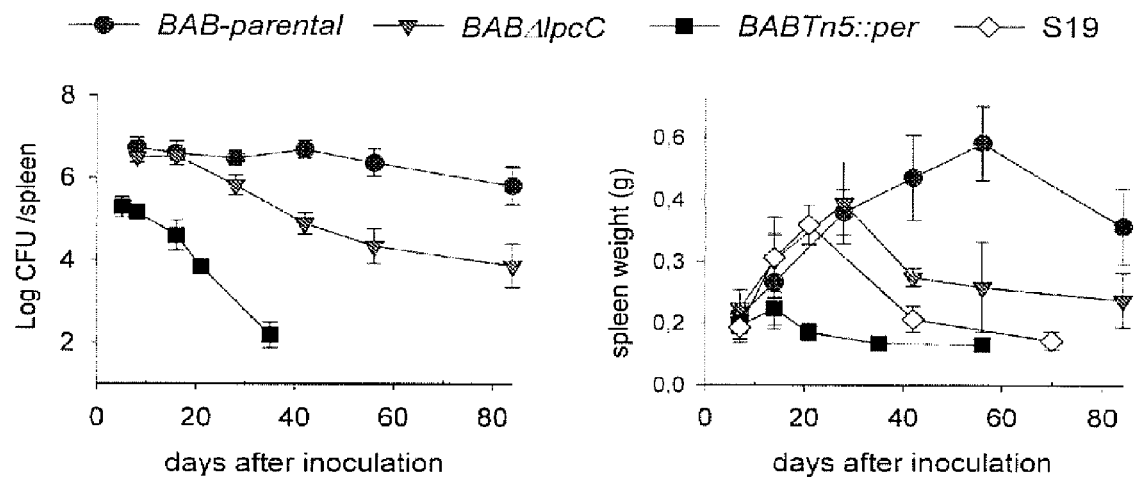
FIG. 9: BABΔlpcC attenuated in mice. The plots show the infection kinetics in the spleens (left panel) and the spleen weights (right panel) of mice inoculated with BAB-parental or BABΔlpcC (each point is the mean±standard error [n=5] of the logarithm of CFU). The plots of the *B. abortus* S19 reference vaccine and of the O-chain deficient BABTn5::per obtained in an independent experiment are added as a reference.
Figure 10:
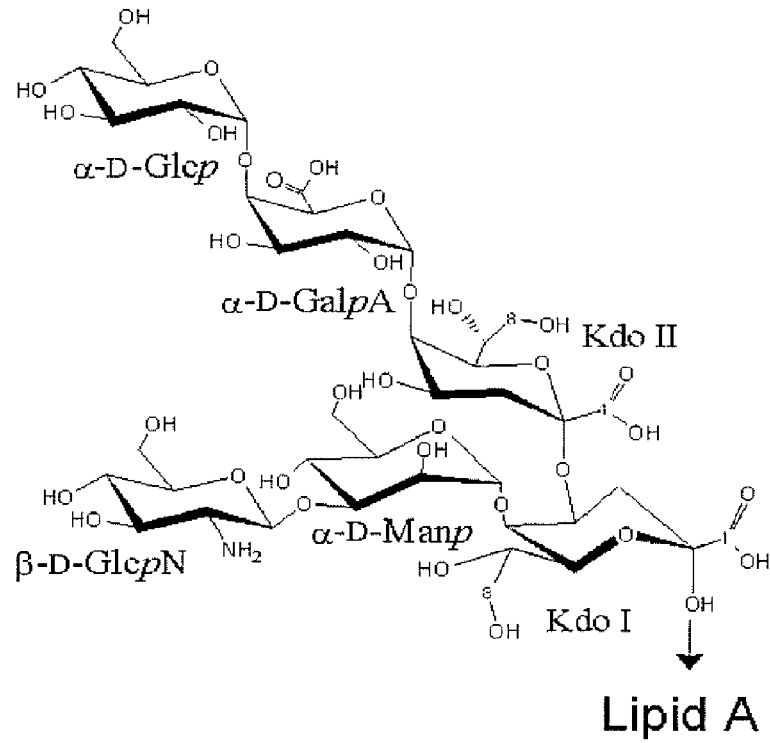
FIG. 10: Proposed representation of the core of *Brucella* LPS. In this representation, the branched structure of the core is represented with two sugar units (alpha-D-Manp and beta-D-GlcpN). The core is linked to lipid A through a Kdo I sugar unit, whereas it is linked to the O-chain through an alpha-D-Glcp. This representation is given with a comprehension purpose only and does not bind the inventors with any theory since the exact structure of the core is still unknown to date.

BABΔlpcC was unable to multiply in BMDCs, suggesting that this mutant could be attenuated in the mouse model. To test this hypothesis, BALBc mice were infected intraperitoneally with the BAB parental and BABΔlpcC and the kinetics of bacterial multiplication in the spleen and the spleen weights compared (FIG. 9). BABΔlpcC showed significant (P=0.0002) attenuation from the 4th week onwards. At the 6th week, the CFU/spleen of BAB-parental were 2 logs higher, and this difference did not change at later times. Splenomegaly increased similarly for both bacteria up to the 4th week. However, whereas spleen enlargement reached a maximum at week 8 for BAB-parental, it began to decrease after week 4 for the BABΔlpcC. In an independent experiment, the spleen CFU of the BABΔlpcC-plpcC complemented strain and the BAB parental strain (mean and standard deviation of log CFU 6.74±0.25 and 6.35±0.31, respectively) were not significantly different (P=0.15) at the time tested (8th week). Moreover, both were significantly different from the CFU obtained for BABΔlpcC in this experiment (4.04±0.49; P<0.001). These results clearly indicated that an intact LPS core is required for full virulence of *B. abortus* in mice.

Protection in Mice.

Figure 11:
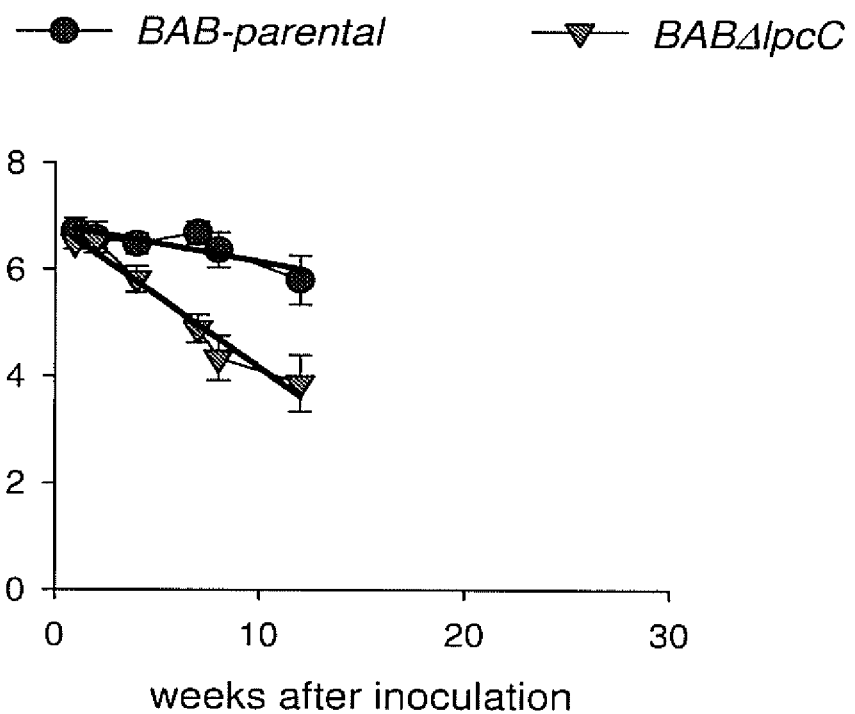
FIG. 11. Regression analysis of the kinetics of spleen clearance of BABΔlpcC and of its parental strain. The corresponding regression equations (y=−0.27x+6.81 [R=0.77] and y 0−0.07x+6.85 [0.95]) predict a clearance time of 25.2 and 93.8 weeks for BABΔlpcC and BAB-parental, respectively. Each point represents the mean±standard error of the logarithm of CFU in the spleens of five animals.

Infection in BMDC triggered a strong IL12 response which is anomalous in mouse brucellosis and could result in a protective Th1 response. This possibility was consistent with the splenomegaly observed because spleen enlargement correlates with the levels of IFN-γ and IL12 in mouse brucellosis (Zhan Y et al. (1993) Infection and Immunity 61: 4899-4901; Zhan Y et al. (1995) Infection and Immunity 63: 1387-1390)

and both cytokines are decisive in generating an effective immunoresponse to *Brucella* (Baldwin C L et al. (2002) Vet Microbiol 90: 367-382). Interestingly, although animals inoculated with BABΔlpcC would eventually clear the infection (FIG. 11), splenomegaly produced by BABΔlpcC was not only greater than that generated by the BABTn5::per mutant but also consistently higher than that induced by the reference vaccine *B. abortus* S19 (FIG. 9), For these reasons, we assed the protection against virulent *B. abortus* induced by vaccination with BABΔlpcC. As it is shown in Table 2, when the spleens were examined 2 weeks after the challenge, BABΔlpcC vaccinated animals contained significantly lower number of CFU/spleen of the challenge strain than the saline control (P<0.001). Moreover, the number of CFU/spleen of the challenge strain were also significantly lower (P=0.025) in the BABΔlpcC vaccinated mice than in the S19 vaccinated ones. The differences between BABΔlpcC and saline vaccinated mice increased six weeks after challenge, and at this time, the immunity afforded by S19 vaccination had completely waned (Table 2).

TABLE 2

Protection against *B. abortus* infection in BALB/c provided by vaccination with BABΔlpcC or *B. abortus* S19

| Vaccine | X $\log_{10}$ CFU in spleen ± SD of virulent *B. abortus* at post-challenge week | |
|---|---|---|
|  | 2 | 6 |
| BABΔlpcC | $1.25 \pm 0.71^{a,b}$ | $0.81 \pm 0.25^{a,c}$ |
| S19 | $3.47 \pm 1.06^{b}$ | $5.27 \pm 0.35^{d}$ |
| Saline | $5.42 \pm 0.51$ | $5.49 \pm 0.12$ |

[a] P versus saline < 0.001.
[b] P versus S19 < 0.05.
[c] P versus S19 < 0.001.
[d] P versus saline > 0.05 (not significant).

Throughout this application, various references describe the state of the art to which this invention pertains. The disclosures of these references are hereby incorporated by reference into the present disclosure.

The invention claimed is:

1. A method for the treatment of brucellosis, comprising the step of administering to a subject in need thereof a therapeutically effective amount of a gram-negative bacterium carrying an inactivated gene encoding a glycosyltransferase involved in the synthesis of the core of the LPS of said gram-negative bacterium,
wherein said glycosyltransferase has the amino acid sequence of SEQ ID NO:1,
wherein said inactivated gene encoding a glycosyltransferase involved in the synthesis of the core of the LPS of said Gram-negative bacterium results in the synthesis of a LPS having a modified core and wherein said Gram-negative bacterium is of the genus *Brucella*.

2. The method according to claim 1, wherein a gene encoding a protein involved in the synthesis of the O-polysaccharide of the LPS is inactivated.

3. The method according to claim 2, wherein said protein involved in the synthesis of the O-polysaccharide of the LPS is a perosamine synthetase having the amino acid sequence of SEQ ID NO:13.

4. The method according to claim 1, wherein said bacteria of the genus *Brucella* is selected from the group consisting of the bacteria of the species *Brucella melitensis, Brucella abortus, Brucella suis, Brucella ovis, Brucella pinnipedialis, Brucella ceti, Brucella microti*, and *Brucella canis*.

5. The method according to claim 1, wherein said bacteria of the genus *Brucella* is of the species *Brucella abortus*.

* * * * *

SEQUENCE LISTING

<160> NUMBER OF SEQ ID NOS: 28

<210> SEQ ID NO 1
<211> LENGTH: 354
<212> TYPE: PRT
<213> ORGANISM: Brucella abortus

<400> SEQUENCE: 1

Met Thr Leu Ser Gly Gln Val Pro Val Arg Glu Val Glu Val Val Ala
1               5                   10                  15

Pro Asn Phe Lys Arg Arg Leu Ser Gly Val Thr Ser Thr Ile Val Gln
            20                  25                  30

Leu Ile Pro Leu Gln Arg Ala Met Gly Leu Lys Ile Ala Thr Met Gly
        35                  40                  45

Pro Gly Leu Pro Asp Thr Leu Pro His Leu Gly Trp Ser Ala Leu Pro
    50                  55                  60

Ser Phe Trp Ser Arg Pro Lys Thr Arg Arg Phe Arg Ile Trp His Ala
65                  70                  75                  80

Arg Arg Asn Ile Glu Met Leu Ala Gly Ile Phe Met Arg Asp Val Leu
                85                  90                  95

Arg Met Lys Leu Arg Leu Val Phe Thr Ser Ala Ala Gln Arg His His
            100                 105                 110

Lys Pro Phe Thr Lys Trp Leu Ile Arg Arg Met Asn Ala Val Ile Ala
        115                 120                 125

Thr Ser Val Arg Ser Gly Ser Phe Leu Glu Val Pro His Gln Val Ile
    130                 135                 140

Met His Gly Val Asp Leu Glu Arg Phe His Pro Pro Leu Ala Glu Asp
145                 150                 155                 160

Asp Asp Phe Ser Ala Ser Gly Leu Pro Gly Lys Tyr Ala Val Gly Cys
                165                 170                 175

Phe Gly Arg Val Arg Pro Ser Lys Gly Thr Asp Leu Phe Val Asp Ala
            180                 185                 190

Met Ile Ala Leu Leu Pro Lys Tyr Pro Asp Trp Thr Ala Ile Val Thr
        195                 200                 205

Gly Arg Thr Thr Ala Glu Tyr Gln Ala Phe Glu Ala Glu Leu Arg Thr
    210                 215                 220

```
Arg Ile Ala Ala Ala Gly Leu Gln Asp Arg Ile Leu Ile Leu Gly Glu
225                 230                 235                 240

Val Pro Asp Val Arg Val Trp Tyr Arg Arg Leu Thr Leu Tyr Val Ala
            245                 250                 255

Pro Ser Arg Asn Glu Gly Phe Gly Leu Thr Pro Leu Glu Ala Met Ala
            260                 265                 270

Ser Lys Thr Ala Val Val Ala Ser Asp Ala Gly Ala Tyr Ala Glu Met
            275                 280                 285

Val Val Glu Asp Thr Gly Arg Phe Val Pro Ala Gly Asp Gly Arg Ala
            290                 295                 300

Leu Thr Asn Ala Ile Glu Pro Tyr Leu Ala Asp Pro Ala Met Thr Lys
305                 310                 315                 320

Arg Cys Gly Glu Asn Ala Leu Ala His Val Arg Glu Ala Phe Pro Leu
                325                 330                 335

Gln Lys Glu Ala Ala Ala Ile Ser Ser Val Tyr Glu Gln Val Phe Ala
            340                 345                 350

Gly Arg

<210> SEQ ID NO 2
<211> LENGTH: 352
<212> TYPE: PRT
<213> ORGANISM: Bartonella quintana

<400> SEQUENCE: 2

Met Arg Met Ser Leu Lys Glu Thr Glu Val Ile Ala Pro His Phe Lys
1               5                   10                  15

Lys Arg Leu Ser Gly Val Thr Ser Thr Val Ile Gln Leu Ile Pro Leu
                20                  25                  30

Gln Arg Lys Gln Gly Ile His Ile Ser Thr Leu Gly Phe Gly Leu Pro
            35                  40                  45

Lys Asn Leu Pro Ala Leu Ala Phe Lys Asp Leu Phe Glu Leu Trp Lys
50                  55                  60

Ser Pro Val Asp Lys Pro Phe Arg Ile Trp His Ala Arg Arg Asn Ile
65                  70                  75                  80

Glu Met Leu Cys Gly Val Phe Leu Arg Asp Ile Leu Arg Met Lys Leu
                85                  90                  95

Lys Leu Leu Phe Thr Ser Ala Ser Arg Arg His His Lys Pro Phe Thr
            100                 105                 110

Lys Trp Leu Ile Arg Arg Met Asp Lys Val Ile Ala Thr Ser Val Cys
            115                 120                 125

Thr Gly Thr Tyr Leu Glu Val Pro His Gln Val Val Met His Gly Val
130                 135                 140

Asp Val Arg Arg Phe Ser Pro Pro Lys Thr Leu Asp Asp Cys Phe Ser
145                 150                 155                 160

Ser Ser Asp Phe Pro Gly Lys Tyr Ala Val Gly Cys Phe Gly Arg Val
                165                 170                 175

Arg Tyr Leu Lys Gly Thr Asp Leu Phe Val Asn Ala Met Ile Ala Leu
            180                 185                 190

Leu Pro Arg Tyr Pro Glu Trp Thr Ala Leu Ile Ala Gly Arg Thr Thr
            195                 200                 205

Glu Gln His Tyr Asn Phe Glu Lys Lys Leu Arg Gln Lys Ile Ala Glu
210                 215                 220

Ala Glu Leu Asp Asn Arg Ile Ile Phe Leu Gly Glu Val Leu Asn Thr
225                 230                 235                 240
```

```
Pro Leu Trp Tyr Arg Arg Leu Ser Leu Tyr Val Thr Pro Ser Arg Leu
                245                 250                 255

Glu Gly Phe Gly Leu Thr Pro Leu Glu Ala Met Ala Ser Gln Thr Ala
            260                 265                 270

Val Val Thr Ser Asp Val Gly Ile Phe Lys Glu Leu Val Glu Gly
            275                 280                 285

Thr Gly Thr Val Val Gln Ala Gly Asp Gly Val Ala Leu Thr Glu Ala
290                 295                 300

Ile Glu Pro Tyr Phe Ala Asp Leu Glu Lys Thr Leu Val Ala Gly Glu
305                 310                 315                 320

Lys Ala Leu Ala His Val Arg Thr His Phe Pro Leu Glu Lys Glu Ala
                325                 330                 335

Ala Glu Ile Gly Ser Ile Tyr Glu Thr Met Phe Ser Gly Lys Thr Leu
            340                 345                 350
```

<210> SEQ ID NO 3
<211> LENGTH: 352
<212> TYPE: PRT
<213> ORGANISM: Bartonella tribocorum

<400> SEQUENCE: 3

```
Met Arg Val Ser Leu Glu Glu Thr Glu Ile Ile Ala Pro His Phe Lys
1               5                   10                  15

Arg Pro Leu Ser Gly Glu Thr Ser Thr Ile Val Gln Leu Val Pro Leu
                20                  25                  30

Met Arg Glu Gln Gly Val Arg Ile Ser Thr Leu Gly Val Gly Leu Pro
            35                  40                  45

Lys Lys Met Pro Ala Leu Ala Phe Arg Asp Leu Phe Gly Leu Trp Lys
        50                  55                  60

Ser Pro Lys Gly Lys Ser Phe Arg Ile Trp His Ala Arg Arg Asn Ile
65                  70                  75                  80

Glu Met Leu Cys Gly Ile Phe Leu Arg Asp Ile Leu Lys Met Lys Leu
                85                  90                  95

Lys Leu Ile Phe Thr Ser Ala Ser Gln Arg His His Lys Pro Phe Thr
            100                 105                 110

Lys Trp Leu Ile Arg Arg Met Asp Arg Val Ile Ala Thr Ser Thr His
        115                 120                 125

Thr Gly Ala Tyr Leu Glu Val Pro His Lys Val Ile Met His Gly Val
130                 135                 140

Asp Val Arg Arg Phe Thr Pro Pro Gln Thr His Asp Asp Cys Phe Ala
145                 150                 155                 160

Ser Thr Gly Phe Pro Gly Lys Tyr Ala Val Gly Cys Phe Gly Arg Val
                165                 170                 175

Arg Tyr Leu Lys Gly Thr Asp Leu Phe Val Glu Ala Met Ile Ala Leu
            180                 185                 190

Leu Pro His Tyr Pro Glu Trp Thr Ala Leu Ile Ala Gly Arg Thr Thr
        195                 200                 205

Glu Gln His Tyr His Phe Glu Lys Glu Leu Arg Gln Lys Ile Ala Lys
210                 215                 220

Ala Gly Leu Asp Asp Arg Ile Ile Phe Leu Gly Glu Ile Leu Asp Ile
225                 230                 235                 240

Pro Leu Trp Tyr Arg Arg Leu Ser Leu Tyr Val Thr Pro Ser Arg Leu
                245                 250                 255

Glu Gly Phe Gly Leu Thr Pro Leu Glu Ala Met Ala Ser Gln Val Ala
            260                 265                 270
```

```
            260                 265                 270
Val Val Thr Ser Asp Val Gly Ile Phe Lys Glu Leu Val Glu Gly
            275                 280                 285

Thr Gly Thr Val Val Lys Val Gly Asp Gly Ser Ala Leu Thr Ala Ala
            290                 295                 300

Ile Glu Pro Tyr Phe Ala Asp Val Glu Lys Thr Leu Ala Ala Gly Lys
305                 310                 315                 320

Lys Ala Leu Thr His Val Arg Thr His Phe Pro Leu Glu Lys Glu Ala
                325                 330                 335

Asn Glu Ile Glu Ser Val Tyr Lys Glu Leu Phe Ala Gly Lys Ile Pro
                340                 345                 350

<210> SEQ ID NO 4
<211> LENGTH: 352
<212> TYPE: PRT
<213> ORGANISM: Bartonella bacilliformis

<400> SEQUENCE: 4

Met His Val Ser Leu Lys Glu Thr Asp Ile Ile Val Pro His Phe Lys
1               5                   10                  15

Lys Arg Leu Ser Gly Ile Lys Ser Thr Val Ile Gln Leu Ile Pro Leu
                20                  25                  30

Gln Arg Lys Gln Gly Ile Arg Ile Ser Ser Phe Gly Val Gly Leu Pro
            35                  40                  45

Lys Asn Leu Pro Thr Leu Arg Val Arg Asp Ile Phe Gly Leu Trp Lys
50                  55                  60

Ser Pro Ala Gly Lys Ser Phe Arg Val Trp His Ala Arg Arg Asn Ile
65                  70                  75                  80

Glu Met Leu Val Gly Val Phe Leu Arg Asp Val Leu Arg Met Lys Leu
                85                  90                  95

Arg Leu Val Phe Thr Ser Ala Ser Glu Arg His His Lys Phe Ser Thr
            100                 105                 110

Arg Trp Leu Ile Arg Arg Met Asp Glu Val Ile Ala Val Ser Ser Arg
            115                 120                 125

Val Gly Thr Tyr Leu Asn Val Pro Tyr Thr Val Ile Lys His Gly Val
            130                 135                 140

Asn Leu Glu Asn Phe Ser Pro Pro Lys Thr Ala Tyr Asp Tyr Phe Ser
145                 150                 155                 160

Ala Thr Gly Leu Pro Gly Lys Tyr Ala Val Gly Cys Phe Gly Arg Ile
                165                 170                 175

Arg Tyr Leu Lys Gly Thr Asp Leu Phe Val Asp Ala Met Leu Ala Leu
            180                 185                 190

Leu Pro Arg Tyr Pro Asp Trp Thr Ala Ile Ala Gly Arg Thr Thr
            195                 200                 205

Met Gln His Cys Asp Phe Glu Lys Glu Leu Arg Arg Lys Ile Ala Ala
            210                 215                 220

Ala Gly Leu Asn Asp Arg Ile Ile Met Leu Gly Glu Ile Leu Asp Thr
225                 230                 235                 240

Pro Leu Trp Tyr Arg Arg Met Ser Leu Tyr Val Ala Pro Ser Arg Thr
                245                 250                 255

Glu Gly Phe Gly Leu Thr Pro Leu Glu Ala Met Ala Ser Gln Thr Ala
            260                 265                 270

Val Val Thr Ser Asp Ala Gly Ile Tyr Glu Lys Leu Ile Val Glu Gly
            275                 280                 285
```

```
Thr Gly Thr Val Val Lys Glu Leu Asn Ala Leu Ala Phe Thr Glu Ala
    290                 295                 300

Ile Glu Pro Tyr Phe Ala Asp Leu Asp Lys Thr Phe Ala Thr Glu Gln
305                 310                 315                 320

Arg Ala Leu Ala His Val Arg Thr His Phe Pro Leu Glu Lys Glu Ala
                    325                 330                 335

Ala Glu Ile Gly Ala Val Tyr Glu Lys Ile Phe Ala Ala Lys Met Phe
                340                 345                 350

<210> SEQ ID NO 5
<211> LENGTH: 340
<212> TYPE: PRT
<213> ORGANISM: Ochrobactrum anthropi

<400> SEQUENCE: 5

Met Ala Pro Asn Phe Lys Arg Arg Leu Ser Gly Val Thr Ser Thr Ile
1               5                   10                  15

Val Gln Leu Ile Pro Leu Gln Arg Ala Lys Gly Leu Asn Ile Ala Thr
            20                  25                  30

Met Gly Pro Gly Leu Pro Asp Thr Leu Pro His Leu Gly Arg Ser Ala
        35                  40                  45

Leu Trp Ser Phe Trp Ser Lys Pro Ala Thr Lys Pro Phe Arg Ile Trp
    50                  55                  60

His Ala Arg Arg Asn Ile Glu Met Leu Ala Gly Ile Phe Met Arg Asp
65                  70                  75                  80

Val Leu Arg Met Lys Leu Arg Leu Ile Phe Thr Ser Ala Ala Gln Arg
                85                  90                  95

Asp His Lys Pro Phe Thr Lys Trp Leu Ile Arg Arg Met Asn Ala Val
                100                 105                 110

Ile Ala Thr Ser Gly Arg Ser Gly Ser Phe Leu Glu Val Pro His Gln
            115                 120                 125

Val Ile Met His Gly Val Asp Leu Glu Arg Phe His Pro Pro Val Gly
        130                 135                 140

Asp Glu Asp Ser Phe Ala Ala Ser Gly Leu Pro Gly Lys Tyr Ala Val
145                 150                 155                 160

Gly Cys Phe Gly Arg Val Arg Ser Ser Lys Gly Thr Asp Leu Phe Val
                165                 170                 175

Asp Ala Met Ile Ala Leu Leu Pro Gln Tyr Pro Asp Trp Thr Ala Ile
                180                 185                 190

Ile Thr Gly Arg Thr Thr Ala Glu His Gln Ser Phe Glu Asp Ala Leu
            195                 200                 205

Lys Ala Lys Ile Ala Ala Ala Gly Leu Gln Asp Arg Ile Leu Ile Leu
        210                 215                 220

Gly Glu Val Pro Asp Ile Arg Val Trp Tyr Arg Arg Leu Thr Leu Tyr
225                 230                 235                 240

Val Ala Pro Ser Arg Asn Glu Gly Phe Gly Leu Thr Pro Leu Glu Ala
                245                 250                 255

Met Ala Ser Gln Thr Ala Val Val Ala Ser Asp Ala Gly Ala Tyr Ala
                260                 265                 270

Glu Met Ile Val Glu Gly Thr Gly Thr Ser Val Ala Ala Gly Asp Gly
            275                 280                 285

Asp Ala Leu Arg Lys Ala Ile Glu Pro Tyr Leu Ala Asp Pro Ala Leu
        290                 295                 300

Ala Glu Arg Asp Gly Glu Asn Ala Leu Arg His Val Arg Ala Thr Phe
305                 310                 315                 320
```

Pro Leu Glu Lys Glu Ala Ala Ala Ile Ser Ala Val Tyr Glu Arg Val
            325                 330                 335

Phe Ala Gly Lys
        340

<210> SEQ ID NO 6
<211> LENGTH: 350
<212> TYPE: PRT
<213> ORGANISM: Ochrobactrum intermedium

<400> SEQUENCE: 6

Met Lys Val Arg Val Gln Asp Val Val Ala Pro Asn Phe Lys
1               5                   10                  15

Arg Arg Leu Ser Gly Val Thr Ser Thr Ile Val Gln Leu Ile Pro Leu
            20                  25                  30

Gln Arg Ala Lys Gly Leu Asn Ile Ala Thr Met Gly Pro Gly Leu Pro
        35                  40                  45

Asp Thr Leu Pro His Leu Gly Trp Gly Ala Leu Leu Ser Phe Trp Ser
    50                  55                  60

Lys Pro Arg Thr Lys Pro Phe Arg Ile Trp His Ala Arg Arg Asn Ile
65                  70                  75                  80

Glu Met Leu Ala Gly Ile Phe Met Arg Asp Val Leu Arg Met Lys Leu
                85                  90                  95

Arg Leu Ile Phe Thr Ser Ala Ala Gln Arg Asp His Lys Pro Phe Thr
            100                 105                 110

Lys Trp Leu Ile Arg Arg Met Asn Ala Val Ile Ala Thr Ser Gly Arg
        115                 120                 125

Ser Gly Ser Phe Leu Gln Val Pro His Asp Val Ile Met His Gly Val
    130                 135                 140

Asp Leu Gln Arg Phe His Pro Pro Val Gly Asp Asp Ser Phe Ala
145                 150                 155                 160

Ala Ser Gly Leu Pro Gly Lys Tyr Ala Val Gly Cys Phe Gly Arg Val
                165                 170                 175

Arg Ser Ser Lys Gly Thr Asp Leu Phe Val Asp Ala Met Val Ala Leu
            180                 185                 190

Leu Pro Lys Tyr Pro Asp Trp Thr Ala Ile Ile Thr Gly Arg Thr Thr
        195                 200                 205

Ala Glu His Gln Ser Phe Glu Asp Ala Leu Lys Ala Lys Ile Ala Ala
    210                 215                 220

Ala Gly Leu Gln Asp Arg Ile Leu Ile Leu Gly Glu Val Pro Asp Ile
225                 230                 235                 240

Arg Val Trp Tyr Arg Arg Leu Thr Leu Tyr Val Ala Pro Ser Arg Asn
                245                 250                 255

Glu Gly Phe Gly Leu Thr Pro Leu Glu Ala Met Ala Ser Gln Thr Ala
            260                 265                 270

Val Val Ala Ser Asp Ala Gly Ala Tyr Ala Glu Met Ile Val Asp Gly
        275                 280                 285

Thr Gly Thr Ser Val Ala Ala Gly Asp Gly Glu Ala Leu Arg Lys Ala
    290                 295                 300

Val Glu Pro Tyr Leu Ala Asp Pro Ala Leu Glu Arg Asp Gly Glu
305                 310                 315                 320

Asn Ala Leu Arg His Val Arg Ala Thr Phe Pro Leu Glu Lys Glu Ala
                325                 330                 335

Ala Ala Ile Ser Gly Val Tyr Glu Arg Val Phe Ala Gly Lys

<210> SEQ ID NO 7
<211> LENGTH: 351
<212> TYPE: PRT
<213> ORGANISM: Agrobacterium tumefaciens

<400> SEQUENCE: 7

Met Ser His Val Ser Leu Lys Asp Val Gln Val Leu Ala Pro Asn Phe
1               5                   10                  15

Lys Arg Arg Leu Ser Gly Val Thr Ser Thr Ile Val Gln Leu Ile Pro
            20                  25                  30

Val Gln Asn Arg Leu Gly Gln Lys Val Gly Thr Ile Gly Pro Gly Leu
        35                  40                  45

Pro Pro His Leu Pro His Val Arg Phe Arg Asp Leu Trp Arg Leu Trp
    50                  55                  60

Gln Asn Gly Pro Ser Gly Pro Arg Ile Trp His Ala Arg Arg Asn
65                  70                  75                  80

Leu Glu Met Leu Pro Gly Ile Phe Met Arg Asp Val Leu Arg Met Lys
                85                  90                  95

Val Lys Leu Leu Phe Thr Ser Ala Ala Gln Arg Arg His Ser Ala Tyr
            100                 105                 110

Thr Arg Phe Leu Ile Ser Lys Met Asp Ala Val Val Ala Thr Ser Thr
        115                 120                 125

Arg Ser Gly Ser Phe Leu Glu Val Pro His Arg Val Val Met His Gly
    130                 135                 140

Val Asp Thr Glu Leu Phe His Pro Ala Thr Gly Pro Glu Asp Thr Ile
145                 150                 155                 160

Ala Ala Thr Gly Leu Pro Gly His Tyr Leu Leu Gly Cys Phe Gly Arg
                165                 170                 175

Val Arg His Gln Lys Gly Thr Asp Leu Phe Val Arg Ala Met Ile Glu
            180                 185                 190

Leu Leu Pro His Tyr Pro Gln Trp Thr Ala Val Val Ser Gly Arg Val
        195                 200                 205

Thr Ala Glu His Lys Ala Phe Gly Asp Thr Leu Lys Ala Asp Val Ala
    210                 215                 220

Ala Ala Gly Leu Thr Asp Arg Ile Ile Phe Gln Gly Glu Val Asp Asp
225                 230                 235                 240

Ile Lys Pro Trp Tyr Arg Arg Leu Thr Leu Tyr Val Ala Pro Ser Arg
                245                 250                 255

Asn Glu Gly Phe Gly Leu Thr Pro Leu Glu Ala Met Ala Ser Glu Thr
            260                 265                 270

Ala Val Val Ala Ser Asn Ala Gly Ala Tyr Glu Glu Met Ile Val Thr
        275                 280                 285

Gly Glu Thr Gly Trp Val Val Gly Ala Gly Asp Tyr Ala Ser Leu Arg
    290                 295                 300

Asp Ala Ile Lys Thr Tyr Leu Ala Asp Pro Ala Leu Ala Lys Ala His
305                 310                 315                 320

Ala Ser Ala Gly Leu Ala His Val Arg Ser Thr Phe Pro Leu Glu Lys
                325                 330                 335

Glu Ala Thr Cys Leu Gly Glu Val Tyr Glu Ala Leu Gln Arg Gly
            340                 345                 350

<210> SEQ ID NO 8
<211> LENGTH: 519

<212> TYPE: PRT
<213> ORGANISM: Brucella melitensis

<400> SEQUENCE: 8

```
Met Asn Lys Leu Gly Val Phe Ile Gly Tyr Asn Pro Gly Gln Leu Asp
1               5                   10                  15

Pro Tyr Gln Gly Ile Ser Arg Leu Ile Ala Phe Val Ile Lys Gly Ala
            20                  25                  30

Leu Asn Gln Gly Ser Gly Val Thr Ile Ala Cys Pro Gly Trp Leu Lys
        35                  40                  45

Asp Asp Val Arg Val Leu Leu Glu Asp Ala Asp Ile Pro Leu Glu Ala
    50                  55                  60

Val Lys Ile Ile Ala Thr Asn Gly Gln Pro Pro Leu Ala Ser Leu Trp
65                  70                  75                  80

Lys Leu Arg Asp Lys Phe Arg Lys Arg Thr Ser Lys Arg Lys Arg
                85                  90                  95

Leu Trp Leu Glu Arg Tyr Gly Lys Asn Val Ala Asn Phe Val Ala Glu
            100                 105                 110

Trp Leu Ser Leu Arg Ser Tyr Trp Gly Ile Phe Leu Gly Ala Ala Ala
        115                 120                 125

Ile Ala Val Val Thr Ile Leu Leu Ala Val Pro Ile Ala Ile Ala Phe
    130                 135                 140

Thr Ala Leu Ile Gly Leu Leu Phe Ala Arg Arg Leu Ile Arg Arg Val
145                 150                 155                 160

Ile Arg Ser Lys Leu Gly Leu Phe Phe His Lys Asn Ala Asn Gln Phe
                165                 170                 175

Asn Lys Leu Met Ser Ser Asp Glu Thr Ile Asp Arg Met Arg Glu Arg
            180                 185                 190

Glu Phe Ser Leu Leu Met Lys Lys Ile Asn Ala Gln Lys Asp Ile Lys
        195                 200                 205

Val Trp Tyr Val Pro Ala Met Phe Trp Pro Glu Val Ala Asn Ile Lys
    210                 215                 220

Ser Lys Ile Val Met Ala Ala Pro Asp Ile Val Phe Phe Asp Tyr Pro
225                 230                 235                 240

Gly Asn Phe Arg Gly Ile Arg Glu His Asn Ser Tyr Asp Arg Met Leu
                245                 250                 255

Lys Ser Leu Arg Ser Ala Asp His Leu Val Cys Tyr Ser Glu Asn Ala
            260                 265                 270

Lys Gln Lys His Phe Val Glu Arg Cys Asp Val Pro Ala Glu Lys Ile
        275                 280                 285

Thr Val Ile Arg His Gly Phe Val Asp Leu Gly Ala Ser Gly Ala Ala
    290                 295                 300

Ile Leu Arg Gln Asp Ala Leu Asp Thr Leu His Ala Phe Ile Lys Lys
305                 310                 315                 320

Asn Asp Gly Arg Met Pro Glu Tyr Leu Lys Gly Phe Arg Phe Asp Asp
                325                 330                 335

Val Pro Phe Phe Phe Tyr Ser Ser Gln Leu Arg Pro His Lys Asn Ile
            340                 345                 350

Glu Gly Leu Ile Arg Ala Tyr Ala Lys Val Leu Lys Glu His Gln Arg
        355                 360                 365

Pro Ala Lys Leu Ile Leu Thr Ala Gln Phe Gly Tyr Asp Lys Arg Ile
    370                 375                 380

Gln Thr Phe Ile Asp Asp Asn Gly Leu His Ala Asp Val Leu Ser Leu
385                 390                 395                 400
```

```
His Ser Leu Pro Asn Lys Val Leu Ala Ala Leu Tyr His Leu Ala Ser
                405                 410                 415

Leu Ser Val Thr Pro Thr Asn Phe Glu Gly Gly Phe Pro Phe Thr Phe
            420                 425                 430

Ser Glu Ala Tyr Ser Val Gly Thr Pro Ser Ile Met Ser Arg Ile Pro
        435                 440                 445

Val Val Gln Glu Val Ile Asp Asp Pro Glu Leu Gln Asp Leu Met Thr
    450                 455                 460

Phe Asn Pro Leu Asp Val Asp Asp Ile Ala Asn Lys Met Ile Phe Gly
465                 470                 475                 480

Leu Asp Asn Arg Gln Arg Leu Phe Glu Ala Gln Ser Ser Leu Tyr Ala
                485                 490                 495

Lys Leu Ser Ala Arg Thr Trp Gln Val Ala Ala Asn Asp Tyr Leu Ser
            500                 505                 510

Leu Leu Lys Ser Val Ala Asp
        515

<210> SEQ ID NO 9
<211> LENGTH: 410
<212> TYPE: PRT
<213> ORGANISM: Brucella melitensis

<400> SEQUENCE: 9

Met Ala Pro Arg His Ile Thr Val Ile Leu Pro Ala Lys Tyr Arg Gly
1               5                   10                  15

Gly Ser Leu Arg Val Thr Lys Asn Ile Val Arg Met Leu Leu Lys Gly
            20                  25                  30

Ser Gln Asn Tyr Gly Glu Gln Cys Gln Val Arg Leu Ala Val Arg Ala
        35                  40                  45

Asp Thr Tyr Asp Ile Gly Glu Glu Phe Arg Asp Leu Ile Asp Asn Gly
    50                  55                  60

Val Glu Val Arg Glu Ile Ser Phe Lys Glu Val Pro Pro Glu Asp Val
65                  70                  75                  80

Asn Asn Ala Asn Tyr Phe Gln Gly Arg Asn Ile Asp Leu Gln Ser Arg
                85                  90                  95

Thr Tyr Trp Leu Met Glu Asp Gly Gln Asn Asn Cys Ala Asp Ser Asp
            100                 105                 110

Leu Trp Leu Val Val Ser Tyr Ser Val Glu Tyr Pro Ile Ala Pro Ile
        115                 120                 125

Arg Pro Thr Leu Ile Phe Ala Thr Asp Phe Ile Gln Arg Tyr Val Pro
    130                 135                 140

Asp Ile Ile Trp Pro Pro Arg Pro Gly Glu Gly Asp Ala Glu Ala Leu
145                 150                 155                 160

Ala Phe Leu Arg Gln Ser Asp Gly Val Leu Ala Thr Thr Pro His Thr
                165                 170                 175

Arg Leu Asp Ala Ile Ser Tyr Ala Gly Leu Pro Ala Ser Lys Val Tyr
            180                 185                 190

Leu Ala Pro Met Glu Phe Asp Pro Thr Phe Leu Asp Arg Tyr Arg Ser
        195                 200                 205

Val Ser Lys Val Lys Glu Pro Tyr Phe Leu Trp Pro Thr Asn Pro Asn
    210                 215                 220

Ala His Lys Asn His Ala Lys Ala Phe Gln Ala Leu Asp Leu Tyr Tyr
225                 230                 235                 240

Gly Lys Leu Lys Gly Lys Ile Lys Thr Lys Ile Val Gly Val Ser Ser
```

-continued

```
                245                 250                 255

Val Arg Met Asp Pro Ser His Arg Trp Gln Ala Lys Tyr Glu Asn Lys
            260                 265                 270

Ala Tyr Val Lys Ser Val Arg Glu Ile Val Ala Gly Leu Asp Asn Leu
        275                 280                 285

Lys Ser Asn Val Glu Phe Ala Gly Glu Val Ala Asp Lys Glu Tyr Ala
    290                 295                 300

Glu Leu Leu Ala Ser Ala Cys Phe Leu Trp His Pro Thr Leu Ala Asp
305                 310                 315                 320

Asn Gly Thr Phe Ala Ala Val Glu Ala Ala Tyr Met Gly Cys Pro Thr
                325                 330                 335

Leu Ser Asn Asp Tyr Pro Gln Met Arg Tyr Ile Ser Asn Arg Phe Glu
            340                 345                 350

Ile Pro Met Gln Tyr Phe Asn Ala Arg Ser Val Lys Glu Met Ala Ser
        355                 360                 365

Ala Leu Lys Gln Met Glu Glu Thr Pro Ile Asp Val Gly Leu Leu Pro
    370                 375                 380

Ser Arg Glu Thr Leu Ser Leu His Ser Trp Glu Ala His Ala Ser Glu
385                 390                 395                 400

Tyr Trp Asp Val Ile Val Arg Ala Ala Ala
                405                 410

<210> SEQ ID NO 10
<211> LENGTH: 377
<212> TYPE: PRT
<213> ORGANISM: Brucella melitensis

<400> SEQUENCE: 10

Met Pro His Leu Tyr Trp Arg Asn Met Arg Val Leu His Phe Phe Lys
1               5                   10                  15

Thr Tyr Trp Pro Asp Thr Phe Gly Gly Ile Glu Arg Thr Ile His Ala
            20                  25                  30

Ile Ala Lys Gly Val Ala Glu His Gly Ile Ala Ser Asp Val Leu Ser
        35                  40                  45

Leu Ser Ala Lys Pro Glu Glu Asn Thr Arg Asn Phe Asp Gly His Met
    50                  55                  60

Ala Tyr Lys Ala Lys Leu Asp Leu Glu Phe Ala Ser Thr Gly Leu Ser
65                  70                  75                  80

Arg Asp Val Phe Ser Arg Phe Arg Glu Leu Ser Ser Gln Ala Asp Val
                85                  90                  95

Ile His Tyr His Phe Pro Trp Pro Met Ser Asp Ile Val Gln Ile Gly
            100                 105                 110

Val Arg Pro Asp Lys Pro Thr Ile Val Thr Tyr His Ser Asp Ile Val
        115                 120                 125

Lys Gln Lys Leu Leu Leu Gln Phe Tyr Arg Pro Leu Met Asn Arg Phe
    130                 135                 140

Leu Gly Ser Val Asp Arg Ile Val Ala Thr Ser Pro Asn Tyr Leu Ala
145                 150                 155                 160

Thr Ser Asp Val Leu Gln Arg Phe Ser Asp Lys Thr Thr Val Ile Pro
                165                 170                 175

Leu Gly Leu Asp Glu Ser Asp Tyr Ser Ala Ala Asp Ala Thr Thr Lys
            180                 185                 190

Ala Arg Trp Arg Glu Arg Phe Pro Arg Pro Phe Phe Leu Phe Val Gly
        195                 200                 205
```

Val Leu Arg Tyr Tyr Lys Gly Leu Arg Thr Leu Leu Ala Ala Ala Arg
210                 215                 220

Thr Ser Asp Ile Asp Ile Val Ile Val Gly Asp Gly Pro Met Lys Pro
225                 230                 235                 240

Gln Leu Ile Ala Tyr Ala Asn Glu His Asn Leu Ser His Val His Phe
            245                 250                 255

Ala Gly Ala Leu Pro Asp Thr Asp Lys Thr Ala Leu Leu Glu Leu Ser
        260                 265                 270

Ala Gly Leu Ile Phe Pro Ser His Leu Arg Ser Glu Ala Phe Gly Leu
            275                 280                 285

Ser Leu Val Glu Ala Ser Met Phe Gly Lys Pro Met Ile Ser Cys Glu
290                 295                 300

Ile Gly Thr Gly Thr Ser Tyr Val Asn Leu Asn Gly Gln Thr Gly Ile
305                 310                 315                 320

Val Val Pro Pro Gln Asn Pro Glu Ala Leu Ser Ala Ala Met Arg Ser
                325                 330                 335

Ile Ala His Asp Thr Glu Gln Ala Lys Val Phe Gly Met Asn Ala Arg
            340                 345                 350

Ala Arg Tyr Ile Glu His Phe Thr Ala Asp Lys Met Ala Leu Glu Tyr
        355                 360                 365

Ala Lys Asn Tyr Thr Ser Leu Met Gln
370                 375

<210> SEQ ID NO 11
<211> LENGTH: 372
<212> TYPE: PRT
<213> ORGANISM: Brucella melitensis

<400> SEQUENCE: 11

Met Arg Ile Gly Val Asp Ala Arg Asn Leu Val Asn Asn Ile Thr Gly
1               5                   10                  15

Ile Ser Arg Tyr Val Met Glu Asn Cys Arg Glu Leu Tyr Glu Arg Gly
            20                  25                  30

His Glu Leu Val Leu Tyr Thr Pro Glu Lys Pro Arg Val Gln Leu Ser
        35                  40                  45

Ser Ser Glu Gly Phe Asp Phe Arg Val Ser Asn Phe Gln Gly Pro Ala
    50                  55                  60

Gly Arg Leu Phe Trp Ser Gln Thr Val Leu Pro Leu Gln Leu Arg Lys
65                  70                  75                  80

Asp Arg Ile Asp Val Phe Trp Gly Pro Ala His Arg Leu Pro Ala Leu
                85                  90                  95

Lys Gly Ala Ile Pro Ser Val Val Ser Ile His Asp Leu Val Trp Tyr
            100                 105                 110

Tyr Ala Ser Ser Thr Met Arg Leu Gln Gly Trp Leu Ala Asp Arg Phe
        115                 120                 125

Leu Met Lys Gly Ala Leu Arg Asn Ala Asp Gln Ile Val Ala Val Ser
130                 135                 140

Tyr Ala Thr Ser Ser Ala Ile Ser Ser Val Phe Pro Gln Tyr Thr Ser
145                 150                 155                 160

Lys Ile Gln Met Val Tyr Pro Gly Val Ser His Phe Asn Arg Ile Gly
                165                 170                 175

Thr Ser Asn Ile Leu Lys Glu His Arg Ile Asn Lys Ser Tyr Gly Leu
            180                 185                 190

Phe Ile Gly Thr Leu Glu Pro Arg Lys Asn Leu Ile Arg Leu Leu Glu
        195                 200                 205

-continued

Ala Tyr Ala Asn Leu Pro Glu Cys Val Arg Asn Asn Phe Leu Leu Val
        210                 215                 220

Val Ala Gly Gly Lys Gly Trp Asn Leu Gly Asp Ile Gly Lys Thr Ile
225                 230                 235                 240

Asn Arg Leu Gly Ile Ala Glu Tyr Thr Arg Leu Thr Gly Tyr Val Thr
                245                 250                 255

Asp Ser Asp Leu Asn Asp Leu Tyr Arg Asn Ala Arg Thr Leu Leu Met
                260                 265                 270

Pro Ser Leu Tyr Glu Gly Phe Gly Leu Pro Ile Ile Glu Ala Gln Ala
            275                 280                 285

Tyr Gly Val Pro Val Ile Thr Ser Asn Cys Ser Ser Met Pro Glu Val
290                 295                 300

Ala Gly Asp Ala Ala Ile Leu Val Asp Pro Leu Asn Val Ala Glu Ile
305                 310                 315                 320

Ser Asn Ala Leu Tyr Arg Ile Ala Thr Asp Asn Lys Leu Trp Gln Arg
                325                 330                 335

Lys Ser Leu Leu Ala Leu Gln Asn Ile Glu Arg Phe Asn Trp His Asn
                340                 345                 350

Ser Ile Glu Lys Leu Glu Ser Val Phe Ile Lys Ala Arg Glu Ser Lys
            355                 360                 365

Leu Met Thr Tyr
        370

<210> SEQ ID NO 12
<211> LENGTH: 362
<212> TYPE: PRT
<213> ORGANISM: Brucella melitensis

<400> SEQUENCE: 12

Met Lys Lys Val Ala Leu Ile Thr Gly Ile Thr Gly Gln Asp Gly Ala
1               5                   10                  15

Tyr Leu Ala Glu Leu Leu Leu Gln Lys Gly Tyr Ala Val His Gly Ile
                20                  25                  30

Lys Arg Arg Thr Ser Gln Phe Asn Thr Ala Arg Ile Asp His Leu Tyr
            35                  40                  45

His Asp Pro His Glu Gln Gly Val Asp Leu Thr Leu His His Gly Asp
        50                  55                  60

Leu Thr Asp Thr Ser Ser Leu Val Arg Ile Met Gln Leu Val Arg Pro
65                  70                  75                  80

Asp Glu Val Tyr Asn Leu Gly Ala Gln Ser His Val Ala Val Ser Phe
                85                  90                  95

Glu Glu Pro Glu Tyr Thr Ala Asn Ser Asp Ala Leu Gly Ala Leu Arg
            100                 105                 110

Leu Leu Glu Ala Ile Arg Ile Leu Gly Met Glu Lys Gln Thr Arg Tyr
        115                 120                 125

Tyr Gln Ala Ser Thr Ser Glu Leu Tyr Gly Leu Val Gln Glu Ile Pro
    130                 135                 140

Gln Lys Glu Thr Thr Pro Phe Tyr Pro Arg Ser Pro Tyr Ala Ala Ala
145                 150                 155                 160

Lys Leu Tyr Ala Tyr Trp Ile Thr Val Asn Tyr Arg Glu Ala Tyr Gly
                165                 170                 175

Ile Tyr Ala Cys Asn Gly Ile Leu Phe Asn His Glu Ser Pro Leu Arg
            180                 185                 190

Gly Glu Thr Phe Val Thr Arg Lys Ile Thr Arg Ala Leu Ala Arg Ile

```
        195                 200                 205

Lys Ile Gly Asn Gln Asn Arg Leu Tyr Leu Gly Asn Leu Asp Ser Leu
    210                 215                 220

Arg Asp Trp Gly His Ala Arg Asp Tyr Val Glu Met Gln Trp Leu Met
225                 230                 235                 240

Leu Gln Gln Asp Gln Pro Glu Asp Phe Val Ile Ala Thr Gly Lys Gln
                245                 250                 255

Tyr Ser Val Arg Glu Phe Val Thr Leu Ala Ala Lys Asp Ile Gly Ile
            260                 265                 270

Glu Met Arg Trp Glu Gly Ser Gly Glu Ala Glu Lys Gly Tyr Asp Ala
        275                 280                 285

Lys Thr Gly Ala Cys Ile Val Glu Val Asp Pro Arg Tyr Phe Arg Pro
    290                 295                 300

Ala Glu Val Glu Thr Leu Leu Gly Asp Ala Thr Lys Ala His Gln Lys
305                 310                 315                 320

Leu Gly Trp Lys Pro Lys Ile Ser Phe Glu Thr Leu Val Ser Glu Met
                325                 330                 335

Ile Ala Glu Asp Leu Ala Ala Ala Ala Arg Glu Asn Leu Leu Arg Glu
            340                 345                 350

His Gly His Gln Phe Phe Ala Pro Lys Glu
        355                 360

<210> SEQ ID NO 13
<211> LENGTH: 380
<212> TYPE: PRT
<213> ORGANISM: Brucella melitensis

<400> SEQUENCE: 13

Met Val Thr Asn Phe Ser Pro Leu Arg Asn Asp Pro Tyr Met Asp Ile
1               5                   10                  15

Pro Val Tyr Ser Pro Tyr Leu Cys Gly Asn Phe Lys Lys Tyr Val Asn
            20                  25                  30

Glu Cys Leu Asp Thr Gly Trp Ile Ser Ser Arg Gly Glu Phe Ile Ser
        35                  40                  45

Arg Phe Glu Asp Ala Phe Ala Gln Tyr Val Asp Val Pro Ser Ala Ala
    50                  55                  60

Ser Val Ala Asn Gly Thr Val Ala Leu His Leu Ala Leu Asp Ala Leu
65                  70                  75                  80

Gly Ile Gly Ala Gly Asp Glu Val Ile Val Pro Thr Phe Thr Tyr Ile
                85                  90                  95

Ala Ser Val Asn Thr Ile Leu Gln Thr Gly Ala Thr Pro Val Tyr Val
            100                 105                 110

Asp Ser Leu Glu Asn Thr Leu Gln Ile Asp Pro Glu Gly Val Arg Leu
        115                 120                 125

Ala Ile Thr Glu Arg Thr Lys Ala Val Met Val Val His Leu Tyr Gly
    130                 135                 140

His Pro Cys Asp Met Asp Ser Ile Arg Glu Ile Cys Asp Glu Lys Ser
145                 150                 155                 160

Leu Leu Leu Val Glu Asp Cys Ala Glu Gly Phe Gly Thr Lys Trp Lys
                165                 170                 175

Asn Ser His Val Gly Thr Phe Gly Asp Val Ala Thr Phe Ser Phe Phe
            180                 185                 190

Gly Asn Lys Thr Ile Thr Thr Gly Glu Gly Gly Met Val Leu Ala Arg
        195                 200                 205
```

Asn Pro Gln Val Met Glu Lys Cys Arg His Leu Lys Ser Gln Gly Thr
    210                 215                 220

Ser Pro Thr Arg Glu Tyr Trp His Asp Ala Leu Ala Tyr Asn Tyr Arg
225                 230                 235                 240

Met Thr Asn Ile Gln Ala Ala Ile Gly Leu Ser Gln Ile Glu Met Ala
            245                 250                 255

Asp Glu Ile Leu Ser Leu Lys Ala Arg Thr Ala Ala Ser Tyr Ala Ser
            260                 265                 270

Lys Leu Ala Gly Leu Pro Leu Arg Met His Thr Pro Val Gly Asp Val
        275                 280                 285

Lys His Ser Tyr Trp Met Cys Ser Ile Val Leu Asp Asn Ser Glu His
    290                 295                 300

Arg Glu Pro Leu Arg Gln His Leu Arg Glu Asn Gly Val Asp Thr Arg
305                 310                 315                 320

Pro Phe Phe Pro Ala His Arg Met Pro His Ser Ala Ser Thr Gly
            325                 330                 335

Ser Tyr Pro Val Ala Asp Ser Leu Ser Ala Arg Gly Leu Asn Leu Pro
            340                 345                 350

Ser Phe Pro His Ile Thr Asp Val Glu Ile Ser Phe Val Cys Asp Leu
        355                 360                 365

Val Arg Ser Tyr Phe Ser Asn His Ser Asn His Ile
    370                 375                 380

<210> SEQ ID NO 14
<211> LENGTH: 265
<212> TYPE: PRT
<213> ORGANISM: Brucella melitensis

<400> SEQUENCE: 14

Met Arg Arg Phe Arg Met Ile Ser Tyr Met Ala Asn Val Trp Lys Val
1               5                   10                  15

Arg His Phe Trp Trp His Leu Ser Met Ser Asp Leu Arg Gly Arg Phe
            20                  25                  30

Arg Arg Ser Ser Leu Gly Ile Leu Trp Ala Val Ile Gln Pro Leu Ala
        35                  40                  45

Leu Thr Leu Leu Leu Ser Phe Val Phe Ser Lys Leu Leu Asn Gln Ser
    50                  55                  60

Ile Ser Ala Tyr Ala Pro Tyr Ile Leu Ser Gly Ile Ile Ile Trp Glu
65                  70                  75                  80

Tyr Ile Ser Phe Thr Val Val Gly Gly Ser Thr Ala Leu Val Gln Ala
                85                  90                  95

Asp Ala Tyr Ile Lys Gln Thr Arg Asn Pro Leu Ala Ile Tyr Thr Leu
            100                 105                 110

Arg Asn Thr Val Ser Gly Leu Val Val Leu Ser Val Ala Ser Ile Ser
        115                 120                 125

Leu Phe Gly Trp Val Leu Ile Met Phe Pro Glu Asn Phe Ser Leu Ser
    130                 135                 140

Trp Leu Ala Ile Pro Thr Leu Leu Pro Ile Leu Ala Leu Ile Val Trp
145                 150                 155                 160

Pro Leu Ala Thr Ile Val Gly Tyr Ile Gly Ala Arg Phe Arg Asp Leu
                165                 170                 175

Pro Asn Ala Leu Ala Leu Val Leu Gln Ala Ala Trp Phe Val Ser Pro
            180                 185                 190

Val Tyr Phe Lys Glu Ser Met Phe Arg Gln Gly Gly Leu Asn Ala Phe
        195                 200                 205

```
Val Asp Tyr Asn Pro Ile Tyr His Val Met Gln Ile Leu Arg Ala Pro
    210                 215                 220

Val Leu Tyr Gly Glu Trp Pro Thr Ala Thr Asn Tyr Ile Trp Cys Leu
225                 230                 235                 240

Gly Val Ser Leu Leu Leu Thr Cys Val Ala Val Ala Val Gly Met Arg
                245                 250                 255

Ala Glu Lys Arg Ala Ile Phe Tyr Leu
            260                 265

<210> SEQ ID NO 15
<211> LENGTH: 335
<212> TYPE: PRT
<213> ORGANISM: Brucella melitensis

<400> SEQUENCE: 15

Met Arg Phe Leu Leu Val Ser Phe Phe Val Ser Ala Leu Leu Cys Gly
1               5                   10                  15

Ile Gly Leu Phe Leu Leu Ser His Leu Leu Pro Ala Asn Phe Leu Ala
            20                  25                  30

Ala Arg Met Ser Ser Arg Ser Asn His Ser Ile Ala Ala Arg Gln Ile
        35                  40                  45

Gly Gly Leu Ala Leu Ile Pro Ala Ile Leu Val Thr Leu Ala Ile Phe
    50                  55                  60

Ala Pro Asp Leu Glu Val Asn Met Gln Leu Phe Leu Cys Leu Ser Gly
65                  70                  75                  80

Ala Ser Leu Leu Leu Trp Val Val Gly Gly Leu Asp Asp Arg Tyr Glu
                85                  90                  95

Leu Ser Glu Ile Ile Arg Leu Gly Ser Gln Leu Leu Ala Ala Ile Thr
            100                 105                 110

Val Leu Tyr Gly Leu Gly Pro Asp Phe Arg Leu Leu Pro Asn Leu Leu
        115                 120                 125

Pro Tyr Trp Leu Glu Ala Thr Leu Ile Val Phe Ala Leu Ile Ile Ala
    130                 135                 140

Ile Asn Val Thr Asn Phe Met Asp Gly Leu Asp Leu Met Thr Val Ala
145                 150                 155                 160

Gly Leu Gly Val Pro Leu Val Gly Ile Ala Leu Leu Gly Ala Leu Gly
                165                 170                 175

Leu Thr Gly Leu Thr Ser Ser Gly Ile Gly Ala Val Ala Ala Gly Gly
            180                 185                 190

Leu Leu Gly Phe Ala Leu Phe Asn Arg Pro Pro Ala Ser Ile Phe Leu
        195                 200                 205

Gly Asp Ser Gly Ser Pro Pro Leu Gly Leu Ile Val Gly Thr Ala Leu
    210                 215                 220

Leu Leu Leu Ala Arg Glu Thr His Ile Val Val Ala Leu Val Leu Pro
225                 230                 235                 240

Leu Tyr Tyr Ile Leu Asp Ala Gly Thr Thr Ile Val Met Arg Ala Ala
                245                 250                 255

Gln Gly Glu Asn Ile Leu Lys Ala His Ser Lys His Ala Tyr Gln Ile
            260                 265                 270

Ala Lys Arg Ser Gly Trp Ser Val Pro Lys Val Val Ala His Val Ala
        275                 280                 285

Leu Leu Asn Thr Ile Leu Ile Ala Cys Val Val Ala Leu Leu Ala Leu
    290                 295                 300

Asp His Pro Leu Ala Gln Leu Thr Phe Leu Leu Val Ala Ala Val Ala
```

-continued 305 310 315 320

Thr Leu Ile Leu Leu Leu Asp Phe Arg Gly Arg Phe Arg Lys Leu
325 330 335

<210> SEQ ID NO 16
<211> LENGTH: 622
<212> TYPE: PRT
<213> ORGANISM: Brucella melitensis

<400> SEQUENCE: 16

Met Ser Leu Lys Tyr Pro Trp Gln Arg Leu Ala Leu Leu Pro Arg Ile
1 5 10 15

Ser Lys Gln Ile Ile Leu Val Leu Ser Asp Cys Leu Leu Leu Leu Ala
20 25 30

Ser Ala Tyr Leu Ala Phe Val Val Arg Phe Gly Phe Val Phe Val Pro
35 40 45

Asn Leu Ala Gln Leu Phe Leu Ile Leu Ile Ala Pro Leu Leu Ala Ile
50 55 60

Pro Val Phe Ile Arg Phe Gly Leu Tyr Arg Ala Ile Ile Arg Tyr Leu
65 70 75 80

Ala Glu Arg Ala Ile Trp Ser Thr Phe Gln Ala Thr Ala Val Ala Ala
85 90 95

Leu Phe Trp Val Ala Leu Val Phe Leu Met Glu Leu Tyr Gly Ser Thr
100 105 110

Gly Leu Pro Arg Ser Val Pro Leu Leu Tyr Trp Leu Leu Ser Thr Val
115 120 125

Phe Ile Ser Ala Ser Arg Phe Gly Ala Lys Trp Leu Leu Arg Thr Ala
130 135 140

Glu His Asp Lys Arg Tyr Thr Ser Ser Ala Leu Ile Ile Gly Ile Gly
145 150 155 160

Glu Pro Ala Arg Gln Leu Ala Thr Ala Leu Arg Ser His Ser Asp Thr
165 170 175

Leu Val Val Gly Phe Ile Asp Pro Ala Gly Gln Leu Ala Gly Met Asp
180 185 190

Ile Ile Gly Leu Arg Val Tyr Arg Thr Glu Glu Ile Pro Ser Leu Ile
195 200 205

Glu Asn Tyr Gly Ile Lys Gln Val Val Val Ser Glu Pro Ala Leu Glu
210 215 220

Gln Lys Glu Arg Gln Glu Phe Ala Arg Leu Leu Gly Arg Leu Pro Val
225 230 235 240

Asn Thr Arg Ile Leu Pro Pro Ile Ala Asp Leu Thr Ala Gly Lys Tyr
245 250 255

Leu Val Ser Ala Leu Arg Asn Val Glu Ile Asp Asp Leu Leu Gly Arg
260 265 270

Ser Pro Val Pro Pro Asp Thr Thr Leu Leu Arg Glu Val Val Glu Gly
275 280 285

Arg Arg Ile Met Ile Thr Gly Ala Gly Gly Ser Ile Gly Ser Gln Leu
290 295 300

Cys Leu Thr Ile Ala Gln Trp Asn Pro Ala Ala Ile Val Leu Phe Glu
305 310 315 320

Ser Ser Glu Phe Ala Leu Tyr Gln Ile Asp Arg Gln Leu Arg Gln Phe
325 330 335

Ala Ser Cys Thr Val Val Pro Val Leu Gly Ser Val Arg Asp Arg Ala
340 345 350

```
Cys Val Glu Lys Pro Ile Arg Asp His Ser Ile Asp Thr Val Tyr His
            355                 360                 365
Cys Ala Ala Tyr Lys His Val Pro Leu Val Glu Arg Asn Pro Leu Val
    370                 375                 380
Gly Ile Phe Asn Asn Val Phe Gly Thr Leu Glu Val Ala Glu Ala Ala
385                 390                 395                 400
Leu Asn Thr Asp Val Glu Arg Met Val Leu Ile Ser Ser Asp Lys Ala
                405                 410                 415
Val Arg Pro Thr Asn Val Met Gly Ala Thr Lys Arg Trp Ala Glu Leu
            420                 425                 430
Val Val Tyr Tyr Tyr Gly Arg Leu Ala Glu Gln Ala Gly Lys Lys Lys
            435                 440                 445
Ala Phe Tyr Ser Val Arg Phe Gly Asn Val Leu Gly Ser Asn Gly Ser
    450                 455                 460
Val Val Pro Leu Phe Arg Glu Gln Ile Ala Asn Gly Gly Pro Val Thr
465                 470                 475                 480
Leu Thr His Glu Asp Met Thr Arg Tyr Phe Met Ser Ile Lys Glu Ala
                485                 490                 495
Ala Glu Leu Ile Val Gln Ser Gly Ala Ile Ala Gln Ser Gly Asp Thr
            500                 505                 510
Val Leu Leu Glu Met Gly Glu Pro Val Lys Ile Arg Asp Leu Ala Glu
            515                 520                 525
Asn Met Ile Leu Leu Ala Gly Leu Thr Val Arg Asn Glu Glu Asn Pro
    530                 535                 540
Gln Gly Asp Ile Ala Ile Glu Val Thr Gly Ile Arg Glu Gly Glu Lys
545                 550                 555                 560
Met Tyr Glu Glu Leu Phe Tyr Asp Pro Ser Leu Ala Gln Arg Thr Arg
                565                 570                 575
His Pro Lys Ile Met Arg Ala Pro Gln Gly Ser Lys Ala Val Val Asp
            580                 585                 590
Ile Gln Glu Ser Leu Ala Val Leu Arg Thr Ala Met Glu Lys Lys Asp
            595                 600                 605
Ile Glu Met Val Arg Lys Val Leu Phe Glu Val Ile Ala Ser
610                 615                 620

<210> SEQ ID NO 17
<211> LENGTH: 19
<212> TYPE: DNA
<213> ORGANISM: Artificial
<220> FEATURE:
<223> OTHER INFORMATION: Synthetic PCR primer

<400> SEQUENCE: 17
ctggcgtcag caatcagag                                                    19

<210> SEQ ID NO 18
<211> LENGTH: 20
<212> TYPE: DNA
<213> ORGANISM: Artificial
<220> FEATURE:
<223> OTHER INFORMATION: SyntheticPCR primer

<400> SEQUENCE: 18
gtgcaacgac ctcaacttcc                                                   20

<210> SEQ ID NO 19
<211> LENGTH: 40
<212> TYPE: DNA
```

<213> ORGANISM: Artificial
<220> FEATURE:
<223> OTHER INFORMATION: Synthetic PCR primer

<400> SEQUENCE: 19
ggaagttgag gtcgttgcac acgccatcga accttatctg 40

<210> SEQ ID NO 20
<211> LENGTH: 18
<212> TYPE: DNA
<213> ORGANISM: Artificial
<220> FEATURE:
<223> OTHER INFORMATION: Synthetic PCR primer

<400> SEQUENCE: 20
cggctatcgt gcgattct 18

<210> SEQ ID NO 21
<211> LENGTH: 239
<212> TYPE: PRT
<213> ORGANISM: Brucella abortus

<400> SEQUENCE: 21

```
Met Asn Val Lys Ala Phe Ile Ile His Leu Lys Arg Ala Thr Asp Arg
1               5                   10                  15

Ala Pro Gln Val Glu Lys Leu Ile Lys Glu Leu Pro Val Lys Ala Glu
            20                  25                  30

Val Ile Glu Ala Val Asp Ser Arg Ala Leu Asn Lys Asp Glu Ile Ala
        35                  40                  45

Arg Ile Tyr Lys Arg Arg Leu His Thr Pro Arg Tyr Pro Phe Ala Leu
    50                  55                  60

Ser Arg Asn Glu Ile Ala Cys Phe Leu Ser His Arg Lys Ala Trp Gln
65                  70                  75                  80

Ala Ile Ile Asp Arg Lys Leu Asp Ala Gly Phe Ile Val Glu Asp Asp
                85                  90                  95

Ile Ala Leu Thr Glu Asn Phe Met Gly Ala Tyr Arg Ala Ala Val Asp
            100                 105                 110

His Leu Glu Pro Gly Gly Phe Ile Arg Phe Thr Phe Arg Asp Asp Arg
        115                 120                 125

Glu His Gly Arg Glu Val Phe Arg Asp Glu Ala Val Arg Ile Ile Ile
    130                 135                 140

Pro Asn Pro Ile Gly Leu Gly Met Val Ala Gln Phe Val Ser Tyr Asp
145                 150                 155                 160

Ala Ala Gln Lys Leu Leu Asp Ile Thr Gln Thr Phe Asp Arg Pro Val
                165                 170                 175

Asp Thr Thr Val Gln Met Arg Trp Val Thr Gly Leu Gln Pro Leu Ser
            180                 185                 190

Val Ile Pro Gly Gly Val Lys Glu Ile Ser Ser Gln Leu Gly Gly Thr
        195                 200                 205

Thr Ile Gln His Lys Lys Asn Phe Ser Asp Lys Leu Ala Arg Glu Ile
    210                 215                 220

Leu Arg Pro Ile Tyr Arg Met Arg Val Arg Ala Tyr Ser Ser Lys
225                 230                 235
```

<210> SEQ ID NO 22
<211> LENGTH: 352
<212> TYPE: PRT
<213> ORGANISM: Bartonella henselae

<400> SEQUENCE: 22

```
Met His Val Ser Leu Glu Glu Thr Glu Ile Ile Ala Pro His Phe Lys
1               5                   10                  15

Lys Arg Leu Ser Gly Ile Thr Ser Thr Val Val Gln Leu Ile Pro Leu
            20                  25                  30

Gln Arg Lys Gln Gly Ile Arg Ile Ala Thr Phe Gly Phe Gly Leu Pro
        35                  40                  45

Asn Asn Leu Pro Ala Leu Ala Phe Lys Asp Leu Phe Gly Leu Trp Lys
    50                  55                  60

Ser Pro Ile Gly Lys Pro Phe Arg Ile Trp His Ala Arg Arg Asn Ile
65                  70                  75                  80

Glu Met Leu Cys Gly Ile Phe Leu Arg Asp Val Leu Arg Met Lys Leu
                85                  90                  95

Lys Leu Leu Phe Thr Ser Ala Ser Gln Arg His His Lys Ser Phe Thr
            100                 105                 110

Lys Trp Leu Ile Arg Arg Met Asp Lys Val Ile Ala Thr Ser Ile Arg
        115                 120                 125

Thr Gly Thr Tyr Leu Glu Val Pro His Gln Val Ile Met His Gly Val
    130                 135                 140

Asp Val Arg Arg Phe Ser Pro Pro Lys Thr Phe Glu Asp Cys Phe Ser
145                 150                 155                 160

Ser Ser Gly Phe Pro Gly Lys Tyr Ala Val Gly Cys Phe Gly Arg Val
                165                 170                 175

Arg Tyr Ser Lys Gly Thr Asp Leu Phe Val Asp Ala Met Ile Ala Leu
            180                 185                 190

Leu Pro Arg Tyr Pro Glu Trp Thr Ala Leu Ile Ala Gly Arg Thr Ile
        195                 200                 205

Glu Gln His Tyr Tyr Phe Glu Lys Lys Leu Arg Gln Lys Ile Ala Glu
    210                 215                 220

Ala Gly Leu Asn Asp Arg Ile Val Phe Leu Gly Glu Val Leu Asn Thr
225                 230                 235                 240

Pro Leu Trp Tyr Arg Arg Leu Ser Leu Tyr Val Ala Pro Ser Arg Thr
                245                 250                 255

Glu Gly Phe Gly Leu Thr Pro Leu Glu Ala Met Ala Ser Gln Thr Ala
            260                 265                 270

Val Val Ala Ser Asp Ala Gly Ala Tyr Lys Glu Leu Val Val Glu Gly
        275                 280                 285

Thr Gly Thr Ile Val Gln Ala Gly Asp Gly Gly Ala Leu Thr Ala Ala
    290                 295                 300

Ile Glu Pro Tyr Phe Ala Asp Leu Glu Lys Thr Met Ala Ala Gly Glu
305                 310                 315                 320

Lys Ala Leu Ala His Val Arg Thr His Phe Pro Leu Glu Lys Glu Ala
                325                 330                 335

Ala Ala Ile Arg Asn Val Tyr Glu Thr Val Phe Ala Gln Lys Thr Leu
            340                 345                 350
```

<210> SEQ ID NO 23
<211> LENGTH: 255
<212> TYPE: PRT
<213> ORGANISM: Ochrobactrum anthropi

<400> SEQUENCE: 23

```
Met Asn Glu Thr Arg Pro Asp Ile Thr Ala Asn Asp Gly Pro Gln Arg
1               5                   10                  15
```

```
Ala Val Lys Ala Phe Ile Ile His Leu Glu Arg Ala Thr Asp Arg Gln
             20                  25                  30

Pro Gln Val Glu Glu Leu Val Arg Arg Leu Pro Val Glu Thr Asp Val
         35                  40                  45

Val Asn Ala Val Asp Gly Arg Thr Leu Asp Ala Gln Thr Ile Ser Arg
     50                  55                  60

Val Tyr Arg Arg Ser Ala His Lys Pro Arg Tyr Pro Phe Gln Leu Ser
65                  70                  75                  80

Thr Asn Glu Ile Ala Cys Phe Leu Ser His Arg Lys Ala Trp Gln Ala
                 85                  90                  95

Ile Val Asp Gln Glu Leu Asp Ala Gly Leu Val Leu Glu Asp Asp Val
             100                 105                 110

Glu Leu Thr Pro Glu Phe Ala Ala Ala Tyr Ser Ala Ala Cys Gln Ile
         115                 120                 125

Leu Lys Ala Asp Ser Phe Ile Arg Phe Pro Phe Arg Glu Arg Glu Ser
     130                 135                 140

Gly Arg Val Val Leu Asn Thr Glu Thr Leu Arg Ile Ile Glu Pro Val
145                 150                 155                 160

Pro Val Gly Leu Gly Met Val Ala Gln Leu Val Gly Arg Glu Ala Ala
                 165                 170                 175

Gln Arg Leu Leu Ser Ala Thr Glu Val Phe Asp Arg Pro Val Asp Thr
             180                 185                 190

Thr Ala Gln Met Asn Trp Val Thr Gly Leu Lys Pro Leu Ser Val Leu
         195                 200                 205

Pro Gly Gly Val Lys Glu Ile Ser Val Gln Leu Gly Gly Ser Thr Ile
     210                 215                 220

Gln Lys Ser Arg Ser Leu Pro Asp Lys Leu Lys Arg Glu Ile Leu Arg
225                 230                 235                 240

Pro Leu Tyr Arg Trp Lys Ile Lys Ser Arg Ser Arg Ala Ala Ile
                 245                 250                 255

<210> SEQ ID NO 24
<211> LENGTH: 255
<212> TYPE: PRT
<213> ORGANISM: Ochrobactrum intermedium

<400> SEQUENCE: 24

Met Asn Glu Thr Arg Pro Asp Ile Thr Ala Ser Asp Gly Pro Gln Arg
1               5                  10                  15

Ala Val Lys Ala Phe Ile Ile His Leu Glu Arg Ala Thr Asp Arg Gln
             20                  25                  30

Pro Gln Val Glu Ala Leu Ile Arg Lys Leu Pro Ile Glu Thr Asp Val
         35                  40                  45

Val Asn Ala Val Asp Gly Arg Thr Leu Asp Ala Gln Thr Ile Ser Arg
     50                  55                  60

Val Tyr Arg Arg Ser Ala His Lys Pro Arg Tyr Pro Phe Gln Leu Ser
65                  70                  75                  80

Thr Asn Glu Ile Ala Cys Phe Leu Ser His Arg Lys Ala Trp Gln Ala
                 85                  90                  95

Ile Val Asp Gln Gly Leu Asp Ala Gly Leu Val Leu Glu Asp Asp Val
             100                 105                 110

Glu Leu Thr Pro Glu Phe Ala Ala Ala Tyr Ser Ala Ser Cys Gln Leu
         115                 120                 125

Leu Lys Ala His Ser Phe Ile Arg Phe Pro Phe Arg Glu Arg Glu Ser
     130                 135                 140
```

```
Gly Arg Val Val Leu Thr Thr Glu Gly Val Arg Ile Ile Glu Pro Val
145                 150                 155                 160

Pro Val Gly Leu Gly Met Val Ala Gln Leu Val Gly Arg Glu Ala Ala
                165                 170                 175

Gln Arg Leu Leu Ser Ala Thr Glu Val Phe Asp Arg Pro Val Asp Thr
            180                 185                 190

Thr Ala Gln Met Asn Trp Val Thr Gly Leu Lys Pro Leu Ser Val Leu
        195                 200                 205

Pro Gly Gly Val Lys Glu Ile Ser Val Gln Leu Gly Gly Ser Thr Ile
210                 215                 220

Gln Lys Ser Arg Ser Leu Pro Asp Lys Leu Lys Arg Glu Ile Leu Arg
225                 230                 235                 240

Pro Leu Tyr Arg Trp Lys Ile Lys Ser Arg Ser Arg Ala Ala Val
                245                 250                 255

<210> SEQ ID NO 25
<211> LENGTH: 278
<212> TYPE: PRT
<213> ORGANISM: Agrobacterium radiobacter

<400> SEQUENCE: 25

Met Gln Thr Tyr Lys Ile Gly Phe Ser Ala Ala Ala Pro Leu Glu Arg
1               5                   10                  15

Ala His Ala Gly Leu Glu Pro Asp Gln Val Pro Leu Gly Thr Ile Asn
            20                  25                  30

Ala Arg Pro Ala Gln Ala Asn Ile Arg Gly Phe Ile Ile His Leu Asp
        35                  40                  45

Arg Ala Arg Asp Arg Leu Pro Gln Val Glu Arg Leu Ala Ala Met Leu
    50                  55                  60

Pro Val Arg Ser Asp Ile Ile Gln Ala Val Asp Ala Ser Ala Phe Pro
65                  70                  75                  80

Asp Ala Asp Ile Asp Leu Val Tyr Arg Arg His Leu His Thr Pro Arg
                85                  90                  95

Tyr Pro Phe Glu Met Ser Val Gly Glu Ile Ala Cys Phe Leu Ser His
            100                 105                 110

Arg Lys Ala Trp Ala Ala Ile Val Glu Gln Gly Val Asp Ala Gly Leu
        115                 120                 125

Val Phe Glu Asp Asp Val Glu Ile Asp Ala Ser Phe His Ala Ala Phe
    130                 135                 140

Ala Ala Ala Gln Ala Cys Leu Thr Pro Gly Ala Phe Ile Arg Phe Pro
145                 150                 155                 160

Phe Arg Met Gly Lys Glu His Gly Glu Cys Val Leu Thr His Gly Gln
                165                 170                 175

Ala Ser Val Ile Gln Pro Gly Arg Val Gly Leu Gly Met Val Ala Gln
            180                 185                 190

Leu Val Ser Arg Asp Ala Ala Ile Arg Leu Leu Glu Ala Thr Ala Leu
        195                 200                 205

Phe Asp Arg Pro Val Asp Thr Thr Val Gln Met Arg Trp Ile Thr Gly
    210                 215                 220

Leu Ser Pro Leu Ala Val Leu Pro Gly Gly Val His Glu Ile Ser Ser
225                 230                 235                 240

Gln Leu Gly Gly Ser Thr Ile Lys Ser Arg Lys Thr Val Phe Glu Lys
                245                 250                 255

Leu Ser Arg Glu Ile Leu Arg Pro Leu Tyr Arg Ala Lys Ile Ala Ile
```

```
            260                 265                 270

Arg Ser Arg Arg Ser Ser
        275

<210> SEQ ID NO 26
<211> LENGTH: 252
<212> TYPE: PRT
<213> ORGANISM: Brucella melitensis 16M

<400> SEQUENCE: 26

Met Ile Gln Pro Ser Ile Thr Leu Ser Asn Val His Leu His Tyr Ala
1               5                   10                  15

Ala Ser Ala Phe Lys Glu Arg Ser Val Lys Thr Leu Val Asn Ala Leu
            20                  25                  30

Leu Ser Met Arg Arg Ser Ala Gly Ala Asn Ile Glu Asp Ile His Ala
        35                  40                  45

Leu Lys Gly Ile Ser Val Asp Ile Ala Arg Gly Glu Arg Val Ala Leu
    50                  55                  60

Ile Gly His Asn Gly Ala Gly Lys Ser Thr Phe Leu Lys Thr Ile Ala
65                  70                  75                  80

Gly Leu Tyr Pro Ile Ser Ser Gly Thr Leu Lys Val Thr Gly Thr Val
                85                  90                  95

Arg Ser Leu Phe Asp Ile Gly Leu Gly Phe Glu Pro Asp Ala Thr Gly
            100                 105                 110

Arg Glu Asn Ile Leu Tyr Arg Gly Leu Leu Leu Gly Leu Thr Pro Arg
        115                 120                 125

Phe Met Arg Glu Ile Glu Asp Glu Ile Ile Glu Phe Ala Asp Leu Gly
    130                 135                 140

Asp Phe Ile Asp Tyr Pro Ile Lys Thr Tyr Ser Ala Gly Met Gln Val
145                 150                 155                 160

Arg Leu Ala Phe Ala Ile Ser Thr Ala Val Asp Gly Asp Ile Leu Leu
                165                 170                 175

Leu Asp Glu Val Ile Gly Ala Gly Asp Ala Ala Phe Met Thr Lys Ala
            180                 185                 190

Lys Ala Arg Ile Met Asn Met Val Glu Lys Ala Glu Ile Met Val Leu
        195                 200                 205

Ala Ser His Asp Leu Ala Asn Val Arg Gln Leu Cys Thr Arg Ala Leu
    210                 215                 220

Val Phe Lys Ala Gly Thr Ile Ala Phe Asp Gly Arg Val Glu Asp Ala
225                 230                 235                 240

Ile Ser Phe Tyr Asn Ser Gly Met Gly Ala Ile Ala
                245                 250

<210> SEQ ID NO 27
<211> LENGTH: 284
<212> TYPE: PRT
<213> ORGANISM: Brucella melitensis 16M

<400> SEQUENCE: 27

Met Ile Arg Asp Ser Gly Ala Pro Arg Arg Val Leu Trp Leu Leu Asn
1               5                   10                  15

His Thr Thr Leu Arg Glu Cys Glu Val Pro Leu Leu Gln Ser Met Gly
            20                  25                  30

Phe Glu Ile Phe Thr Pro Lys Arg Phe Pro Arg Asn Ser Asp Asn Arg
        35                  40                  45

Ser Ala Ser Val Ser Phe Glu Thr Asp Glu Ser Leu Thr Ile Pro Ala
```

-continued

```
    50                  55                  60

Ser Val Ile Asp Glu Leu Asn Ser Tyr Asp Ser Tyr Gln Ala Pro Val
65                  70                  75                  80

Asn Pro Arg Ile Asp Phe Leu Ile Asn Tyr Tyr Phe Glu Asn Ala Ile
                85                  90                  95

Val Ala Tyr Met Phe Pro Met Phe Thr Gln Ile Ile Ser Arg Phe Lys
            100                 105                 110

Gly Arg Ile Leu Leu Arg Ala Phe Gly Leu Thr Ser Glu Thr Trp Thr
        115                 120                 125

Tyr Phe Asp Phe Ala Asn Phe Val Ala Gly Ser Phe Phe Lys Arg Thr
    130                 135                 140

Trp Met Lys Ala Ser Asn Gln Phe Trp Phe Ala Ala Ser Tyr Ser Ser
145                 150                 155                 160

Leu Ile Glu Ile Glu Pro Asn Phe Ile Arg Glu Arg Thr Val Leu Leu
                165                 170                 175

Pro Val Gly Leu Pro Glu Arg Ile Leu Ala Lys Gln Asp Thr Trp Arg
            180                 185                 190

Gly Gly Asp Lys Arg Ile Met Phe Val Cys Pro Asp Ile Glu Thr Tyr
        195                 200                 205

Pro Glu Ala Lys Ala Ala Tyr Ser Glu Ser Lys His Val Phe Gly Asp
    210                 215                 220

Leu Ser His Val Ile Cys Gly Asn Gln Thr Ile Pro Val Val Asp Asp
225                 230                 235                 240

Asp Asn Val Val Asp Arg Leu Ser Ala Glu Asp Gly Gly Arg Leu Pro
                245                 250                 255

Ile Ala Met Ser Cys Thr Asn Cys Ser Ala Asn Cys Thr Asn Val Thr
            260                 265                 270

Gln Val Gly Met Gln Ser Arg Val Ser Ile Tyr Ala
        275                 280

<210> SEQ ID NO 28
<211> LENGTH: 259
<212> TYPE: PRT
<213> ORGANISM: Brucella melitensis 16M

<400> SEQUENCE: 28

Met Ala Ile Ala Pro Asn Thr Arg Val Leu Val Ala Gly Tyr Gly Leu
1               5                   10                  15

Pro Ala Glu Phe Cys Val Thr Thr Leu Ile Gly Met Gly Val Glu Ile
            20                  25                  30

Asp Lys Ile Ala Val Ala Thr His Arg Glu Asp Asn Arg Asn Cys Gly
        35                  40                  45

Leu His Ser Met Leu Arg Leu Arg Asn Ile Gln Phe Thr Thr Ala Ala
    50                  55                  60

Ala Asn Ser Glu Glu Phe Tyr Glu Phe Gly Ala Asn Phe Asp Pro Asp
65                  70                  75                  80

Met Ile Ile Ser Met His Tyr Arg Ser Leu Ile Pro Gly Arg Phe Leu
                85                  90                  95

Lys Leu Ala Lys Lys Gly Ser Val Asn Leu His Pro Ser Leu Leu Pro
            100                 105                 110

Ala Tyr Arg Gly Thr Asn Ser Val Ala Trp Val Ile Ile Asn Gly Glu
        115                 120                 125

Ser Glu Thr Gly Phe Ser Tyr His Arg Met Asp Glu Asn Phe Asp Thr
    130                 135                 140
```

-continued

```
Gly Ala Ile Leu Leu Gln Glu Arg Ile Ser Val Glu Glu Thr Asp Thr
145                 150                 155                 160

Ala Phe Ser Leu Phe His Arg Gln Ile Ala Arg Ala Met Leu Arg Leu
                165                 170                 175

Glu Glu Val Ile Leu Lys Leu Asp Gln Gly Asp Pro Gly Phe Ala Gln
            180                 185                 190

Leu Gly Glu Ala Ser Tyr Tyr Ala Arg Glu Leu Pro Phe Gly Gly Val
        195                 200                 205

Ile Asp Pro Arg Trp Ser Glu Val Gln Ile Asp Arg Phe Ile Arg Ala
    210                 215                 220

Met Phe Phe Pro Pro Phe Pro Pro Ala Val Leu Lys Ile Asp Gly Lys
225                 230                 235                 240

Val Tyr Tyr Val Pro Ser Ile Asp Ile Tyr Arg Ser Leu Met Arg Gly
                245                 250                 255

Ile Pro Ser
```